(12) United States Patent
Singhal et al.

(10) Patent No.: US 9,162,072 B2
(45) Date of Patent: Oct. 20, 2015

(54) IMPLANTABLE MEDICAL DEVICE WITH LUBRICIOUS MATERIAL

(75) Inventors: Ruchika Singhal, Minneapolis, MN (US); Darren A. Janzig, Centerville, MN (US); Carl D. Wahlstrand, Lino Lakes, MN (US); Robert M. Skime, Coon Rapids, MN (US); Paulette C. Olson, Eagan, MN (US); Erik R. Scott, Maple Grove, MN (US); James E. Randall, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 2218 days.

(21) Appl. No.: 11/526,514

(22) Filed: Sep. 25, 2006

(65) Prior Publication Data

US 2007/0074732 A1 Apr. 5, 2007

Related U.S. Application Data

(62) Division of application No. 10/837,276, filed on Apr. 30, 2004.

(51) Int. Cl.
*A61N 1/375* (2006.01)
*A61N 1/36* (2006.01)
*A61N 1/05* (2006.01)

(52) U.S. Cl.
CPC .............. *A61N 1/375* (2013.01); *A61N 1/3605* (2013.01); *A61B 2560/0443* (2013.01); *A61N 1/0526* (2013.01)

(58) Field of Classification Search
CPC .............................. A61N 1/375; A61N 1/3968
USPC ...................................................... 607/36, 63
See application file for complete search history.

(56) References Cited

U.S. PATENT DOCUMENTS 3,310,051 A 3/1967 Schulte
3,522,811 A 8/1970 Schwartz et al.
(Continued)

FOREIGN PATENT DOCUMENTS

DE 3940632 12/1990
EP 1 145 735 A2 10/2001
(Continued)

OTHER PUBLICATIONS

Notification of Transmittal of the International Search Report and the Written Opinion of the International Searching Authority dated Dec. 9, 2004, International Application No. PCT/US2004/022110.
(Continued)

*Primary Examiner* — Christopher D Koharski
*Assistant Examiner* — Natasha Patel
(74) *Attorney, Agent, or Firm* — Shumaker & Sieffert, P.A.

(57) ABSTRACT

An implantable medical device with lubricious material permits implantable medical devices to have a reduced friction between the device and at least a portion of the surrounding tissue. The implantable medical device may have a housing or it may have a housing and a member for providing a smooth interface between the device and the tissue. The lubricious material may be provided on or impregnated in the housing or the member. In some embodiments, the device is configured for implantation in the head of a human body. In other embodiments, the device is configured for implantation between the cranium and the scalp. In some embodiments, the device includes a single module while in other embodiments a plurality of modules are coupled together to provide a smaller profile.

47 Claims, 15 Drawing Sheets

(56) References Cited

U.S. PATENT DOCUMENTS

| | | | |
|---|---|---|---|
| 3,690,325 A | 9/1972 | Kenny |
| 3,720,874 A | 3/1973 | Gorcik et al. |
| 3,724,467 A | 4/1973 | Avery et al. |
| 3,888,260 A | 6/1975 | Fischell |
| 3,913,587 A | 10/1975 | Newash |
| 3,926,198 A | 12/1975 | Kolenik |
| 3,941,135 A | 3/1976 | von Sturm et al. |
| 4,006,748 A | 2/1977 | Schulman |
| 4,010,760 A | 3/1977 | Kraska et al. |
| 4,013,081 A | 3/1977 | Kolenik |
| 4,040,412 A | 8/1977 | Sato |
| 4,094,321 A | 6/1978 | Muto |
| 4,256,115 A | 3/1981 | Bilitch |
| 4,266,552 A | 5/1981 | Dutcher et al. |
| 4,328,813 A | 5/1982 | Ray |
| 4,399,819 A | 8/1983 | Cowdery |
| 4,399,820 A | 8/1983 | Wirtzfeld et al. |
| 4,408,607 A | 10/1983 | Maurer |
| 4,499,907 A | 2/1985 | Kallok et al. |
| 4,503,860 A | 3/1985 | Sams et al. |
| 4,574,780 A | 3/1986 | Manders |
| 4,616,655 A | 10/1986 | Weinberg et al. |
| 4,911,178 A | 3/1990 | Neal |
| 4,928,696 A | 5/1990 | Henderson et al. |
| 4,934,368 A | 6/1990 | Lynch |
| 4,969,899 A | 11/1990 | Cox, Jr. |
| 4,972,846 A | 11/1990 | Owens et al. |
| 5,085,644 A | 2/1992 | Watson et al. |
| 5,116,345 A | 5/1992 | Jewell et al. |
| 5,144,946 A | 9/1992 | Weinberg et al. |
| 5,197,332 A | 3/1993 | Shennib |
| 5,207,218 A | 5/1993 | Carpentier et al. |
| 5,218,959 A | 6/1993 | Fenster |
| 5,220,929 A | 6/1993 | Marquit |
| 5,243,977 A | 9/1993 | Trabucco et al. |
| 5,252,090 A | 10/1993 | Giurtino et al. |
| 5,271,397 A | 12/1993 | Seligman et al. |
| 5,312,440 A | 5/1994 | Hirschberg et al. |
| 5,314,451 A | 5/1994 | Mulier |
| 5,314,453 A | 5/1994 | Jeutter |
| 5,396,813 A * | 3/1995 | Takeuchi et al. ............. 73/865.5 |
| 5,411,538 A | 5/1995 | Lin |
| H1465 H | 7/1995 | Stokes |
| 5,431,695 A * | 7/1995 | Wiklund et al. ................ 607/36 |
| 5,433,734 A | 7/1995 | Stokes et al. |
| 5,455,999 A | 10/1995 | Owens et al. |
| 5,456,698 A | 10/1995 | Byland et al. |
| 5,458,997 A | 10/1995 | Crespi et al. |
| 5,477,855 A | 12/1995 | Schindler et al. |
| 5,480,416 A | 1/1996 | Garcia et al. |
| 5,489,225 A | 2/1996 | Julian |
| 5,554,194 A | 9/1996 | Sanders |
| 5,562,715 A | 10/1996 | Czura et al. |
| 5,571,148 A | 11/1996 | Loeb et al. |
| 5,573,551 A | 11/1996 | Lin et al. |
| 5,613,935 A | 3/1997 | Jarvik |
| 5,638,832 A | 6/1997 | Singer et al. |
| 5,645,586 A * | 7/1997 | Meltzer ...................... 623/11.11 |
| 5,674,260 A | 10/1997 | Weinberg |
| 5,678,559 A | 10/1997 | Drakulic |
| 5,702,430 A | 12/1997 | Slimon et al. |
| 5,741,313 A | 4/1998 | Nason et al. |
| 5,755,743 A | 5/1998 | Volz et al. |
| 5,769,874 A | 6/1998 | Dahlberg |
| 5,776,169 A | 7/1998 | Schroeppel |
| 5,792,067 A | 8/1998 | Karell |
| 5,800,535 A | 9/1998 | Howard, III |
| 5,814,095 A | 9/1998 | Leysieffer et al. |
| 5,836,935 A | 11/1998 | Ashton et al. |
| 5,843,150 A | 12/1998 | Adams et al. |
| 5,873,899 A | 2/1999 | Stutz, Jr. et al. |
| RE36,120 E | 3/1999 | Karell |
| 5,876,424 A | 3/1999 | O'Phelan et al. |
| 5,895,414 A | 4/1999 | Sanchez-Zambrano |
| 5,896,647 A | 4/1999 | Shkuratoff |
| 5,919,215 A | 7/1999 | Haeg et al. |
| 5,935,154 A | 8/1999 | Westlund |
| 5,941,905 A | 8/1999 | Single |
| 5,941,906 A | 8/1999 | Barreras, Sr. et al. |
| 5,954,751 A | 9/1999 | Chen et al. |
| 5,954,757 A | 9/1999 | Gray |
| 5,958,088 A | 9/1999 | Vu et al. |
| 5,984,859 A | 11/1999 | Lesinski |
| 5,991,664 A | 11/1999 | Seligman |
| 6,006,124 A | 12/1999 | Fischell et al. |
| 6,016,449 A | 1/2000 | Fischell et al. |
| 6,016,593 A | 1/2000 | Kyrstein |
| 6,044,304 A | 3/2000 | Baudino |
| 6,061,593 A | 5/2000 | Fischell et al. |
| 6,067,474 A | 5/2000 | Schulman et al. |
| 6,091,979 A | 7/2000 | Madsen |
| 6,112,120 A | 8/2000 | Correas |
| 6,128,538 A | 10/2000 | Fischell et al. |
| 6,131,581 A | 10/2000 | Leysieffer et al. |
| 6,134,474 A | 10/2000 | Fischell et al. |
| 6,154,677 A | 11/2000 | Leysieffer |
| 6,162,487 A | 12/2000 | Darouiche |
| 6,168,580 B1 | 1/2001 | Yardley |
| 6,176,849 B1 * | 1/2001 | Yang et al. ..................... 604/265 |
| 6,176,879 B1 | 1/2001 | Leysieffer et al. |
| 6,205,358 B1 | 3/2001 | Haeg et al. |
| 6,214,032 B1 | 4/2001 | Loeb et al. |
| 6,218,016 B1 | 4/2001 | Tedeschi et al. |
| 6,230,049 B1 | 5/2001 | Fischell et al. |
| 6,242,041 B1 * | 6/2001 | Katoot et al. ................. 427/2.24 |
| 6,248,080 B1 | 6/2001 | Miesel et al. |
| 6,248,126 B1 | 6/2001 | Lesser et al. |
| 6,259,951 B1 | 7/2001 | Kuzma et al. |
| 6,263,225 B1 | 7/2001 | Howard, III |
| 6,266,556 B1 | 7/2001 | Ives et al. |
| 6,269,266 B1 | 7/2001 | Leysieffer |
| 6,272,382 B1 | 8/2001 | Lenarz et al. |
| 6,283,997 B1 | 9/2001 | Garg et al. |
| 6,308,101 B1 | 10/2001 | Gord et al. |
| 6,324,428 B1 | 11/2001 | Weinberg et al. |
| 6,324,433 B1 | 11/2001 | Errico |
| 6,330,468 B1 | 12/2001 | Scharf |
| 6,354,299 B1 | 3/2002 | Fischell et al. |
| 6,356,792 B1 | 3/2002 | Zonenshayn et al. |
| 6,358,281 B1 | 3/2002 | Berrang et al. |
| 6,360,122 B1 | 3/2002 | Fischell et al. |
| 6,366,813 B1 | 4/2002 | DiLorenzo |
| 6,405,079 B1 | 6/2002 | Ansarinia |
| 6,415,184 B1 | 7/2002 | Ishikawa et al. |
| 6,427,086 B1 | 7/2002 | Upton et al. |
| 6,436,422 B1 | 8/2002 | Trogolo et al. |
| 6,445,956 B1 | 9/2002 | Laird et al. |
| 6,456,256 B1 | 9/2002 | Amundson et al. |
| 6,456,886 B1 | 9/2002 | Howard et al. |
| 6,480,743 B1 | 11/2002 | Kirkpatrick et al. |
| 6,490,486 B1 | 12/2002 | Bradley |
| 6,498,951 B1 | 12/2002 | Larson et al. |
| 6,505,077 B1 | 1/2003 | Kast et al. |
| 6,516,227 B1 | 2/2003 | Meadows et al. |
| 6,516,808 B2 | 2/2003 | Schulman |
| 6,517,476 B1 | 2/2003 | Bedoya et al. |
| 6,537,200 B2 | 3/2003 | Leysieffer et al. |
| 6,554,762 B2 | 4/2003 | Leysieffer |
| 6,560,486 B1 | 5/2003 | Frei et al. |
| 6,565,503 B2 | 5/2003 | Leysieffer et al. |
| 6,567,703 B1 | 5/2003 | Thompson et al. |
| 6,575,894 B2 | 6/2003 | Leysieffer et al. |
| 6,597,954 B1 | 7/2003 | Pless et al. |
| 6,618,623 B1 | 9/2003 | Pless et al. |
| 6,626,680 B2 | 9/2003 | Ciurzynski et al. |
| 6,648,914 B2 | 11/2003 | Berrang et al. |
| 6,671,544 B2 | 12/2003 | Baudino |
| 6,726,678 B1 | 4/2004 | Nelson et al. |
| 6,736,770 B2 | 5/2004 | Leysieffer et al. |
| 6,782,292 B2 | 8/2004 | Whitehurst |
| 6,788,974 B2 | 9/2004 | Bardy et al. |
| 6,805,998 B2 | 10/2004 | Jenson et al. |
| 6,850,802 B2 | 2/2005 | Holsheimer |
| 6,882,881 B1 | 4/2005 | Lesser et al. |

(56) References Cited

U.S. PATENT DOCUMENTS

| | | | |
|---|---|---|---|
| 6,899,976 | B2 | 5/2005 | Larson et al. |
| 6,963,780 | B2 * | 11/2005 | Ruben et al. ............ 607/36 |
| 6,977,124 | B2 | 12/2005 | Probst et al. |
| 6,994,933 | B1 | 2/2006 | Bates |
| 7,010,351 | B2 | 3/2006 | Firlik et al. |
| 7,103,415 | B2 | 9/2006 | Probst et al. |
| 7,107,097 | B2 | 9/2006 | Stern et al. |
| 7,110,819 | B1 | 9/2006 | O'Hara |
| 7,212,864 | B2 | 5/2007 | Wahlstrand et al. |
| 7,242,982 | B2 | 7/2007 | Singhal et al. |
| 7,263,401 | B2 | 8/2007 | Scott et al. |
| 7,454,251 | B2 | 11/2008 | Rezai et al. |
| 7,596,399 | B2 | 9/2009 | Singhal et al. |
| 7,702,380 | B1 | 4/2010 | Dean |
| 2001/0033953 | A1 | 10/2001 | Takeuchi et al. |
| 2001/0051819 | A1 | 12/2001 | Fischell et al. |
| 2002/0002390 | A1 | 1/2002 | Fischell et al. |
| 2002/0013612 | A1 | 1/2002 | Whitehurst |
| 2002/0019669 | A1 | 2/2002 | Berrang et al. |
| 2002/0042634 | A1 | 4/2002 | Bardy et al. |
| 2002/0051550 | A1 | 5/2002 | Leysieffer |
| 2002/0059049 | A1 | 5/2002 | Bradbury et al. |
| 2002/0068958 | A1 | 6/2002 | Bardy et al. |
| 2002/0072770 | A1 | 6/2002 | Pless |
| 2002/0077670 | A1 | 6/2002 | Archer et al. |
| 2002/0087201 | A1 | 7/2002 | Firlik et al. |
| 2002/0099412 | A1 | 7/2002 | Fischell et al. |
| 2002/0103510 | A1 | 8/2002 | Bardy et al. |
| 2002/0107546 | A1 | 8/2002 | Ostroff et al. |
| 2002/0147498 | A1 | 10/2002 | Tallarida et al. |
| 2002/0161403 | A1 | 10/2002 | Meadows et al. |
| 2002/0165588 | A1 | 11/2002 | Fraley et al. |
| 2002/0169485 | A1 | 11/2002 | Pless et al. |
| 2002/0177882 | A1 | 11/2002 | DiLorenzo |
| 2003/0004428 | A1 | 1/2003 | Pless et al. |
| 2003/0004546 | A1 | 1/2003 | Casey |
| 2003/0017372 | A1 | 1/2003 | Probst et al. |
| 2003/0040781 | A1 | 2/2003 | Sunderland et al. |
| 2003/0073972 | A1 | 4/2003 | Rosenman et al. |
| 2003/0085684 | A1 | 5/2003 | Tsukamoto et al. |
| 2003/0088294 | A1 | 5/2003 | Gesotti |
| 2003/0091893 | A1 | 5/2003 | Kishiyama et al. |
| 2003/0109903 | A1 | 6/2003 | Berrang et al. |
| 2003/0120320 | A1 | 6/2003 | Solom |
| 2003/0125786 | A1 | 7/2003 | Gliner et al. |
| 2003/0130706 | A1 | 7/2003 | Sheffield et al. |
| 2003/0171787 | A1 | 9/2003 | Money et al. |
| 2003/0204229 | A1 | 10/2003 | Stokes |
| 2003/0233115 | A1 * | 12/2003 | Eversull et al. ........ 606/194 |
| 2004/0015070 | A1 | 1/2004 | Liang et al. |
| 2004/0030245 | A1 | 2/2004 | Noble et al. |
| 2004/0082977 | A1 | 4/2004 | Engmark et al. |
| 2004/0102828 | A1 | 5/2004 | Lowry et al. |
| 2004/0176750 | A1 | 9/2004 | Nelson et al. |
| 2004/0176815 | A1 | 9/2004 | Janzig et al. |
| 2004/0181263 | A1 | 9/2004 | Balzer et al. |
| 2004/0186528 | A1 | 9/2004 | Ries et al. |
| 2004/0243481 | A1 | 12/2004 | Bradbury et al. |
| 2005/0004620 | A1 | 1/2005 | Singhal et al. |
| 2005/0033378 | A1 | 2/2005 | Sheffield et al. |
| 2005/0070971 | A1 | 3/2005 | Fowler et al. |
| 2005/0075679 | A1 | 4/2005 | Gliner et al. |
| 2006/0116743 | A1 | 6/2006 | Gibson et al. |
| 2006/0129205 | A1 | 6/2006 | Boveja et al. |
| 2006/0149336 | A1 | 7/2006 | Meadows |
| 2009/0299164 | A1 | 12/2009 | Singhal et al. |
| 2009/0299165 | A1 | 12/2009 | Singhal et al. |
| 2009/0299380 | A1 | 12/2009 | Singhal et al. |

FOREIGN PATENT DOCUMENTS

| | | |
|---|---|---|
| EP | 1 145 736 A2 | 10/2001 |
| GB | 1 161 579 | 8/1969 |
| WO | WO 92/20402 | 11/1992 |
| WO | WO 99/06108 | 2/1999 |
| WO | WO 99/34758 | 7/1999 |
| WO | WO 00/13743 | 3/2000 |
| WO | WO 00/40295 | 7/2000 |
| WO | WO 01/10369 | 2/2001 |
| WO | WO 01/28622 | 4/2001 |
| WO | WO 01/39830 | 6/2001 |
| WO | WO 01/41858 | 6/2001 |
| WO | WO 01/60450 | 8/2001 |
| WO | WO 01/97906 | 12/2001 |
| WO | WO 02/05590 | 1/2002 |
| WO | WO 02/056637 | 7/2002 |
| WO | WO 02/083207 | 10/2002 |
| WO | WO 02/083208 | 10/2002 |
| WO | WO 02/083233 | 10/2002 |
| WO | WO 03/026739 | 4/2003 |
| WO | WO 03/076012 | 9/2003 |
| WO | WO 2004/043536 | 5/2004 |
| WO | 2004/052459 | 6/2004 |
| WO | WO 2004/052458 | 6/2004 |

OTHER PUBLICATIONS

U.S. Appl. No. 10/731,869, filed Dec. 9, 2003, entitled "Modular Implantable Medical Device."
U.S. Appl. No. 10/731,868, filed Dec. 9, 2003, entitled "Implantation of Low-Profile Implantable Medical Device."
U.S. Appl. No. 10/731,699, filed Dec. 9, 2003, entitled "Coupling Module of a Modular Implantable Medical Device."
U.S. Appl. No. 10/730,873, filed Dec. 9, 2003, entitled "Overmold for a Modular Implantable Medical Device."
U.S. Appl. No. 10/837,319, filed Apr. 30, 2004, entitled "Implantable Medical Device With Anti-Infection Agent."
U.S. Appl. No. 10/731,881, filed Dec. 9, 2003, entitled "Reducing Relative Intermodule Motion in a Modular Implantable Medical Device."
U.S. Appl. No. 10/730,878, filed Dec. 9, 2003, entitled "Lead Connection Module of a Modular Implantable Medical Device."
U.S. Appl. No. 10/730,877, filed Dec. 9, 2003, entitled "Low-Profile Implantable Medical Device."
U.S. Appl. No. 10/731,867, filed Dec. 9, 2003, entitled "Concavity of an Implantable Medical Device."
U.S. Appl. No. 10/731,638, filed Dec. 9, 2003, entitled "Modular Implantable Medical Device."
U.S. Appl. No. 10/835,527, filed Apr. 29, 2004, entitled "Implantation of Implantable Medical Device."
U.S. Appl. No. 10/835,232, filed Apr. 29, 2004, entitled "Explantation of Implantable Medical Device."
U.S. Appl. No. 10/835,233, filed Apr. 29, 2004, entitled "Implantable Medical Device With a Nonhermetic Battery."
U.S. Appl. No. 10/835,548, filed Apr. 29, 2004, entitled "Headset Recharger for Cranially Implantable Medical Devices."
U.S. Appl. No. 10/835,245, filed Apr. 29, 2004, entitled "Battery Housing Configuration."
"Surgical Process," Animation Screenshots from http://www.cochlearamerica.com/800.asp, 7 pgs. (2002).
"Candidates Brochure," http://www.cochlearamerica.com/pdfs/candidatebrochglobal.pdf, 14 pgs. (last printed Aug. 19, 2002).
"Research and Development," http://www.cochlearamericas.com/384.asp, 1 pg. (last printed Feb. 3, 2004).
"The World Leader in cochlear implants—revolutionizing hearing for adults and infants," http://www.cochlear.com, 1 pg. (last printed Feb. 3, 2004).
"Cochlear: innovator of the Nucleus 3 cochlear implant system," http://www.cochlearamericas.com, 1 pg. (last printed Feb. 3, 2004).
"What is a Cochlear Implant," http://www.cochlearamericas.com/What/161.asp, 1 pg. (last printed Feb. 3, 2004).
"ESPrit 3G Speech Processor," http://www.cochlearamericas.com/591.asp, 2 pgs. (last printed Feb. 3, 2004).
"Nucleus 3 System," http://www.cochlearamericas.com/Products/465.asp, 1 pg. (last printed Feb. 3, 2004).
"Internal Components: Nucleus 24 Cochlear Implants," http://www.cochlearamericas.com/374.asp, 1 pg. (last printed Feb. 3, 2004).
"Nucleus 24 Contour," http://www.cochlearamericas.com/568.asp, 2 pgs. (last printed Feb. 3, 2004).

(56) References Cited

OTHER PUBLICATIONS

"Nucleus 24 M," http://www.cochlearamericas.com/372.asp, 1 pg. (last printed Feb. 3, 2004).
"Nucleua 24 K," http://www.cochlearamericas.com/371.asp, 1 pg. (last printed Feb. 3, 2004).
"Nucleus 24 Double Array," http://www.cochlearamericas.com/370.asp, 1 pg. (last printed Feb. 3, 2004).
"Nucleus 24 ABI: Auditory Brainstem Implant," http://www.cochlearamericas.com/373.asp, 2 pgs. (last printed Feb. 3, 2004).
"Nucleus Speech Processors," http://www.cochlearamericas.com/629.asp, 1 pg. (last printed Feb. 3, 2004).
"Sprint: body worn speech processor," http://www.cochlearamericas.com/1010.asp, 1 pg. (last printed Feb. 3, 2004).
"Cochlear," http://www.cochlearamericas.com/Recipients/978.asp, 3 pgs. (last printed Feb. 3, 2004).
Notification of Transmittal of the International Preliminary Report on Patentability dated Apr. 13, 2006, International Application No. PCT/US2004/022110, (9 pgs.).
Answers.com, www.answers.com, defined: discrete components, acessed on Mar. 2, 2007 (2 pages).

\* cited by examiner

IMPLANTABLE MEDICAL DEVICE WITH LUBRICIOUS MATERIAL

RELATED APPLICATIONS

This application is a divisional of U.S. patent application Ser. No. 10/837,276, filed on Apr. 30, 2004, entitled "IMPLANTABLE MEDICAL DEVICE WITH LUBRICIOUS MATERIAL," to Singhal et al. The entire content of U.S. patent application Ser. No. 10/837,276 is incorporated herein by reference.

The following co-pending and commonly-assigned U.S. patent applications are also incorporated herein by reference in their entirety:

1. U.S. patent application Ser. No. 10/731,869, filed on Dec. 9, 2003, entitled "MODULAR IMPLANTABLE MEDICAL DEVICE," to Wahlstrand et al.;
2. U.S. patent application Ser. No. 10/731,868, filed on Dec. 9, 2003, entitled "IMPLANTATION OF LOW-PROFILE IMPLANTABLE MEDICAL DEVICE," to Singhal et al.;
3. U.S. patent application Ser. No. 10/731,881, filed on Dec. 9, 2003, entitled "REDUCING RELATIVE INTERMODULE MOTION IN A MODULAR IMPLANTABLE MEDICAL DEVICE," to Wahlstrand et al.;
4. U.S. patent application Ser. No. 10/731,699, filed on Dec. 9, 2003, entitled "COUPLING MODULE OF A MODULAR IMPLANTABLE MEDICAL DEVICE," to Janzig et al.;
5. U.S. patent application Ser. No. 10/730,877, filed on Dec. 9, 2003, entitled "LOW-PROFILE IMPLANTABLE MEDICAL DEVICE," to Janzig et al.;
6. U.S. patent application Ser. No. 10/731,867, filed on Dec. 9, 2003, entitled "CONCAVITY OF AN IMPLANTABLE MEDICAL DEVICE," to Wahlstrand et al.;
7. U.S. patent application Ser. No. 10/730,878, filed on Dec. 9, 2003, entitled "LEAD CONNECTION MODULE OF A MODULAR IMPLANTABLE MEDICAL DEVICE," to Singhal et al.;
8. U.S. patent application Ser. No. 10/731,638, filed on Dec. 9, 2003, entitled "MODULAR IMPLANTABLE MEDICAL DEVICE," to Wahlstrand et al.;
9. U.S. patent application Ser. No. 10/835,233, filed on Apr. 29, 2004, entitled "IMPLANTABLE MEDICAL DEVICE WITH A NONHERMETIC BATTERY," to Scott et al.;
10. U.S. patent application Ser. No. 10/835,232, filed on Apr. 29, 2004, entitled "EXPLANTATION OF IMPLANTABLE MEDICAL DEVICE," to Singhal et al.;
11. U.S. patent application Ser. No. 10/835,527, filed on Apr. 29, 2004, entitled "IMPLANTATION OF IMPLANTABLE MEDICAL DEVICE," to Singhal et al.;
12. U.S. patent application Ser. No. 10/835,548, filed on Apr. 29, 2004 entitled "HEADSET RECHARGER FOR CRANIALLY IMPLANTABLE MEDICAL DEVICES," to Wahlstrand et al.;
13. U.S. patent application Ser. No. 10/835,245, filed on Apr. 29, 2004, entitled "BATTERY HOUSING CONFIGURATION," to Wahlstrand et al.; and
14. U.S. patent application Ser. No. 10/837,319, filed on Apr. 30, 2004, entitled "IMPLANTABLE MEDICAL DEVICE WITH ANTI-INFECTION AGENT," to Singhal et al.

TECHNICAL FIELD

The invention relates to medical devices, and more particularly, to implantable medical devices that deliver therapy to and/or monitor a patient.

BACKGROUND

Depending on the application for which they are implanted in a patient, implantable medical devices (IMDs) may include a variety of electrical and/or mechanical components. Typically, an IMD includes a rigid housing that houses all of its components, which are generally fragile, to protect the components from forces to which they would otherwise be exposed when implanted within the human body. In order to avoid potentially harmful interactions between the components and bodily fluids, e.g., corrosion, IMD housings are typically hermetically sealed. Many IMD housings are fabricated from Titanium because of its desirable rigidity and biocompatibility.

The size and shape of an IMD housing is dependant on the sizes and shapes of the components of the IMD. Large components common to most IMDs include a battery, a telemetry coil, and a hybrid circuit that includes digital circuits, e.g., integrated circuit chips and/or a microprocessor, and analog circuit components. Attempts have been made to reduce the size of the IMD housing by reducing the size of these components, changing the shape of these components, and organizing these components within the IMD housing to avoid empty space within the housing. Despite these efforts to reduce the size of IMD housings, the size, shape and rigidity of IMD housings still greatly limits the locations within the human body where an IMD can be practically implanted.

Due to these limitations, an IMD is typically implanted within the abdomen, upper pectoral region, or subclavicular region of a patient. Leads or catheters must be used in order to deliver therapy or monitor a physiological parameter at a location of the body other than where the IMD is implanted. Implantation and positioning of leads and catheters can be difficult and time-consuming from the perspective of a surgeon, particularly where the IMD is located a significant distance from the treatment or monitoring site. Moreover, the increased surgical time, increased surgical trauma, and increased amount of implanted material associated with the use of leads and catheters can increase the risk to the patient of complications associated with the implantation of an IMD.

For example, IMDs that are used to treat or monitor the brain, e.g., to deliver deep brain stimulation (DBS) therapy, are implanted some distance away from the brain, e.g., within the subclavicular region of patients. The long leads that connect the implantable medical device to electrodes implanted within the brain require tunneling under the scalp and the skin of the neck, thereby requiring increased surgery and a prolonged amount of time under general anesthesia during the implant procedure. In some cases, tunneling the leads under the scalp and skin of the neck requires an additional surgical procedure under general anesthesia. The lengthy tract along the leads is more susceptible to infection, and the leads can erode the overlying scalp, forcing removal so that the scalp can heal. Further, the long leads running under the scalp and through the neck are more susceptible to fracture due to torsional and other forces caused by normal head and neck movements.

Placement of an IMD nearer to the point of application of the therapy or monitoring (for example, in the head of a human body) often results in implanting the device into small spaces or spaces having somewhat inflexible shapes or surroundings. Such small spaces may result in a tighter fit for the IMD within the surrounding tissue. The tightness of the fit of the IMD into such small spaces or spaces with shape requirements results in increased friction both as the device is inserted and after implantation. In the case of an implant in the head such friction results in erosion of the skin and other tissue associated with the scalp.

SUMMARY

In general, the invention relates to an implantable medical device including a lubricious material on the external surface or impregnated in the external surface for reducing friction between the implantable medical device and the tissue in which it is implanted.

Various embodiments of the invention are presented including a device for implantation in the head of a patient. Some more specific embodiments configure the device for implantation between the cranium and the scalp.

Various embodiments of the invention also include a member coupled to the module or modules for providing a smooth interface between the device and the scalp or the tissue near the scalp. These embodiments include a lubricious material on or impregnated in the member. The member may be any material capable of providing a smooth interface with the tissue. The member can include elastomeric materials, such as silicone, and/or non-elastomeric materials such as polysulfone and polyurethane.

Various embodiments of the invention include a single module while other embodiments include a plurality of interconnected modules. These embodiments include a lubricious material on or impregnated in the housing or member.

Methods of fabricating an implantable medical device including a lubricious material are also presented.

The details of one or more embodiments of the invention are set forth in the accompanying drawings and the description below. Other embodiments of the invention will be apparent from the description and drawings, and from the claims.

DETAILED DESCRIPTION

Figure 1A:
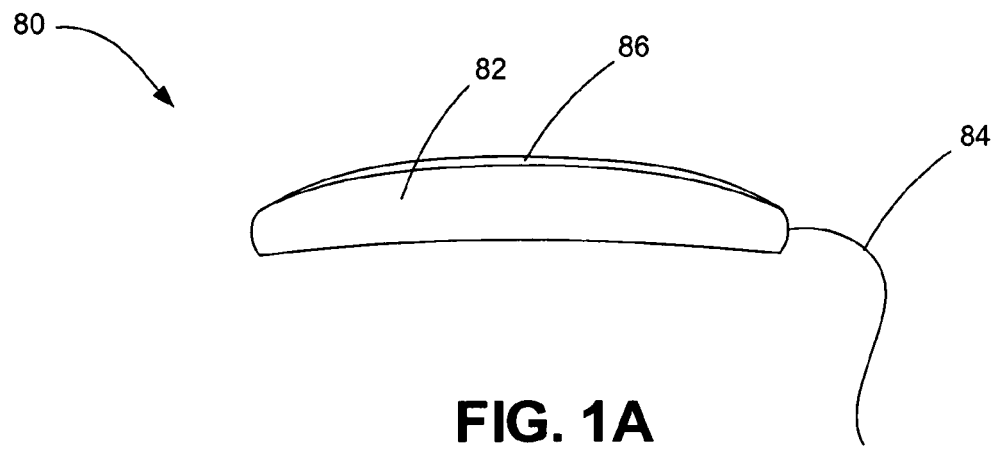
FIG. 1A is a conceptual diagram illustrating one embodiment of an implantable medical device of the present invention.

FIG. 1A is a conceptual diagram of an implantable medical device 80 including housing 82 and therapy delivery element 84. A lubricious material, as described herein, may be disposed on or impregnated in at least a portion of the implantable medical device 80. A lubricious material is any material that when applied to an implantable medical device reduces the friction between the implantable medical device and the adjacent tissue. In one embodiment the lubricious material may be placed on the housing 82 in the form of a coating 86. Disposing a lubricious material on or impregnated in the device 80 may facilitate insertion of the device 80 into the implantable location within a human body. The lubricious material also reduces friction between the device 80 and the tissue near the device 80. In cases where the implantable medical device is implanted in a tight space such as between the cranium and the scalp, the lubricious material may reduce the likelihood of skin erosion by decreasing the friction forces between the device and the scalp. A lubricious material may also minimize fibrous capsule growth around the device by lowering the friction between the device and the scalp. This would have the additional benefit of reducing the likelihood of infection.

For many therapies such as brain stimulation for movement disorders it may be desirable for the device to provide unipolar stimulation whereby the housing is used as an electrode. Therefore, in some embodiments it may be desirable to use a lubricious material that is electrically conductive or to apply the lubricious material to less than the entire housing.

In one embodiment, housing 82 includes at least a portion of the electronics for providing monitoring of or therapy to a patient. Some examples of implantable medical devices that include at least a portion of the electronics for providing monitoring of or therapy to a patient include implantable neurostimulators, implantable drug delivery pumps, pacemakers, defibrillators and monitoring devices that receive physiological signals from a patient and store or relay such information. Such devices that provide therapy to the patient may be open or closed loop devices (e.g., closed loop device receives sensed information and delivers therapy based on the sensed information).

Application of a lubricious material is also desirable in the case of a modular device having more than one module and housing. In such a case a preferred embodiment includes a lubricious material on at least a portion of the housings.

An implantable medical device may be implantable anywhere in the body. For example, the implantable medical device may be implanted in the abdomen, pectoral or buttock areas. An implantable medical device may also be implanted in the head of a patient such as between the cranium and the scalp. Other embodiments may include an implantable medical device for implantation partially or wholly within a groove or recess placed in the cranium.

Figure 1B:
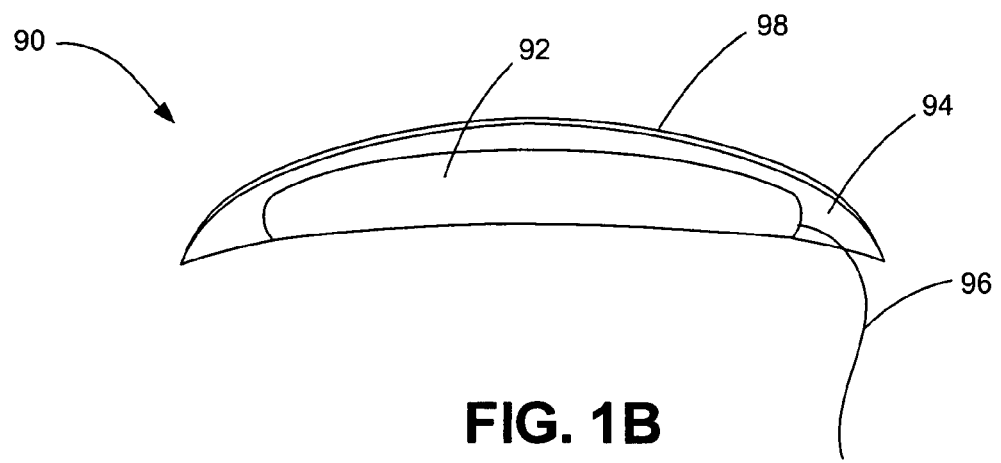
FIG. 1B is a conceptual diagram illustrating another embodiment of an implantable medical device of the present invention.

As shown in FIG. 1B, an implantable medical device may be an implantable medical device 90 for implantation in the head of a patient. Device 90 may be placed between the cranium and the scalp. Device 90 includes housing 92, member 94 and therapy delivery element 96. Member 94 provides a substantially smooth interface between device 90 and the scalp or other tissue near the scalp. In one sub-embodiment of this embodiment, the member 94 partially encapsulates housing 92. A lubricious material may be disposed on or impregnated in the member 94. In one embodiment, the lubricious material is provided as a coating 98 on the member 94. In one embodiment the lubricious material 98 is only on the convex side of the member 94. Application of the lubricious material 98 to the convex side of the member 94 is desired to reduce friction between the convex side of the member 94 and the scalp or other tissue near the scalp. However, the lubricious material may also be applied to more than one side of the member 94.

Figure 1C:
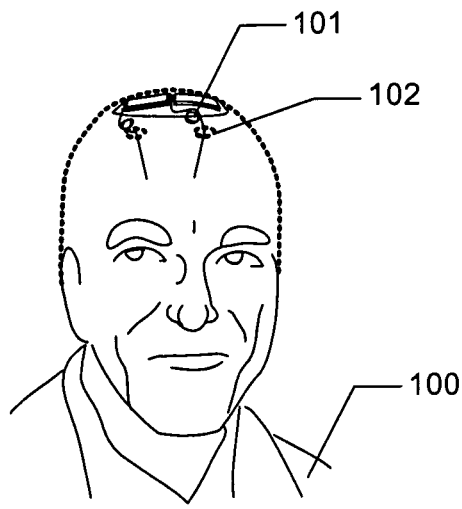
FIGS. 1C and 1D are conceptual diagrams illustrating a modular implantable medical device implanted in a patient according to an example embodiment of the present invention.
Figure 1D:
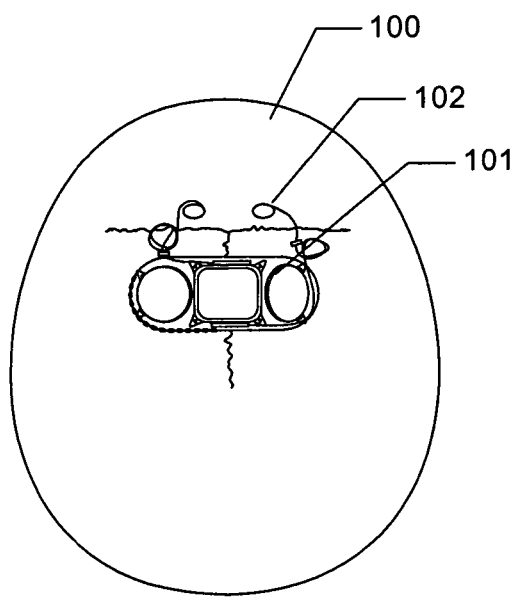

In another embodiment the implantable medical device may be a modular implantable medical device. FIGS. 1C and 1D are conceptual diagrams illustrating a modular implantable medical device 101 implanted within a patient 100. By constructing modular implantable medical device 101 as a set of distributed modules connected together as described herein, modular implantable medical device 101 may be implanted at locations for which implantation of conventional implantable medical devices has been deemed undesirable, thus permitting the implantable medical device 101 to be implanted near a monitoring and/or therapy delivery location. In the example illustrated within FIGS. 1C-1D, modular implantable medical device 101 is implanted under the scalp of the patient 100 in order to locate the device 101 close to the location to which therapy is to be delivered via leads 102, i.e., the brain of patient 100. The low profile and the shape of modular implantable medical device 101 as described herein can reduce the risk of infection and skin erosion associated with implantation of matter beneath the scalp, and may provide a cosmetically acceptable profile when implanted beneath the scalp.

Modular implantable medical device 101 may deliver stimulation to the brain of patient 100 to, for example, provide deep brain stimulation (DBS) therapy, or to stimulate the cortex of the brain. Cortical stimulation may involve stimulation of the motor cortex. Modular implantable medical device 101 may be used to treat any nervous system disorder including, but not limited to, epilepsy, pain, psychological disorders including mood and anxiety disorders, movement disorders (MVD), such as, but not limited to, essential tremor, Parkinson's disease, and neurodegenerative disorders.

However, modular implantable medical device 101 is not limited to delivery of stimulation to the brain of patient 100, and may be employed with leads 102 deployed anywhere in the head or neck including, for example, leads deployed on or near the surface of the cranium, leads deployed beneath the cranium such as near or on the dura mater, leads placed adjacent cranial or other nerves in the neck or head, or leads placed directly on the surface of the brain. Moreover, modular implantable medical device 101 is not limited to implantation under the scalp of patient 100. Indeed, modular implantable medical device 101 may be implanted anywhere within patient 100. For example, modular implantable medical device 101 can be implanted within the neck of patient 100, and deliver stimulation to the vagus nerve or the cervical region of the spinal cord.

Modular implantable medical device 101 may alternatively be implanted within a pectoral region or the abdomen of patient 100 to act as a diaphragmatic pacer, or to provide any of the monitoring and therapy delivery functions known in the art to be associated with cardiac pacemakers. Further, modular implantable medical device 101 may be implanted in the upper buttock region and deliver spinal cord, urological or gastrological stimulation therapy, or may be configured to be implanted within the periphery, e.g., limbs, of patient 100 for delivery of stimulation to the muscles and/or peripheral nervous system of patient 100. As is the case with cranial implantation, the modularity of implantable medical device 101 may enable implantation at some of these example locations for which implantation of conventional implantable medical devices is generally deemed undesirable.

Modular implantable medical device 101 is not limited to embodiments that deliver stimulation. For example, in some embodiments modular implantable medical device 101 may additionally or alternatively monitor one or more physiological parameters and/or the activity of patient 100, and may include sensors for these purposes. Where a therapy is delivered, modular implantable medical device 101 may operate in an open loop mode (also referred to as non-responsive operation), or in a closed loop mode (also referred to as responsive). Modular implantable medical device 101 may also provide warnings based on the monitoring.

As discussed above, the ability of a modular implantable medical device 101 according to the invention to be implanted close to a region within patient 100 to be monitored enables the use of shorter leads 102. Shorter leads 102 may advantageously improve the accuracy of such sensors by reducing noise attributable to leads 102. Shorter leads 102 may also advantageously reduce the negative affects of imaging techniques such as magnetic resonance imaging "MRI" on a person implanted with implantable medical device 101.

Additional alternate embodiments for implantable medical devices implemented according to principles of the present invention may also include non-electrical based therapies such as targeted introduction of fluids and similar therapeutic materials using pumps and reservoirs of material. One skilled in the art will recognize that any number of implantable devices may be possible without deviating from the spirit and scope of the present invention as recited within the attached claims.

Figure 2:
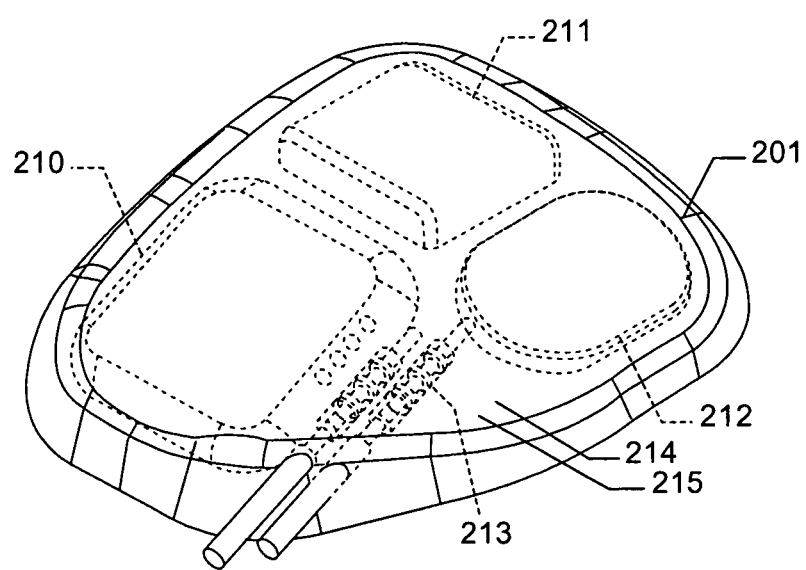
FIG. 2 is a schematic diagram illustrating a modular implantable medical device according to another embodiment of the present invention.

FIG. 2 is a schematic diagram illustrating a modular implantable medical device 201 according to another embodiment of the present invention. In this example embodiment, implantable medical device 201 is arranged in a triangular configuration. Modular implantable medical device 201 includes three modules: a control module 210, a power source module 211, and a recharge module 212. Each of modules 210-212 includes a respective housing. Modular implantable medical device 201 also contains a set of lead connection modules 213 that permits external leads 102 (FIGS. 1C and 1D) to be connected to control module 210 as needed. The distribution of functional components of modular implantable medical device 201 into modules permits modular implantable medical device 201 to possess a thin profile by spreading the components over a larger surface area.

Control module 210 includes control electronics for controlling the monitoring and/or therapy delivery functions of modular implantable medical device 201, such as a microprocessor, and may include therapy delivery circuitry. Power source module 211 includes a power source that provides energy to control module 210, which in some embodiments is a rechargeable power source such as a rechargeable battery and/or capacitor. Recharge module 212 includes a recharge coil for inductively receiving energy to recharge a rechargeable power source within power source module 211.

In some embodiments, one or modules may be coupled by coupling modules (not shown). A coupling module may be flexible, and may include a lumen to carry a conductor or a fluid between modules of a modular implantable medical device. In some embodiments, a coupling module is made of a flexible material such as silicone or a flexible polymer. In other embodiments a coupling module is hermetic and made of substantially less flexible material, such as titanium or stainless steel, and the flexibility of a coupling module is provided by the configuration and/or construction the coupling module.

A coupling module may be flexible in a plurality of directions to provide modules of a modular implantable medical device with multiple degrees of freedom of motion with respect to each other. In exemplary embodiments, a coupling module provides at least three degrees of motion, and the degrees of motion provided include rotational motion.

Additional details regarding modules 210, 211 and 212, additional or alternative modules for a modular implantable medical device, the interconnection of modules within a modular implantable medical device, and lead connection modules 213 may be found in commonly assigned U.S. patent application Ser. No. 10/731,869, entitled "MODULAR IMPLANTABLE MEDICAL DEVICE,"; commonly assigned U.S. patent application Ser. No. 10/731,699, entitled "COUPLING MODULE OF A MODULAR IMPLANTABLE MEDICAL DEVICE,"; and commonly assigned U.S. patent application Ser. No. 10/730,878, entitled "LEAD CONNECTION MODULE OF A MODULAR IMPLANTABLE MEDICAL DEVICE,".

As illustrated in FIG. 2, modular implantable medical device 201 includes a member 214. A member generally serves as a smooth interface between one or more modules and the body tissue.

A member may be made of any material. In one embodiment the member may be made of a metal. For example, a member may be made of titanium or of other biocompatible metals. In another embodiment, the member may be made of a soft, biocompatible material. In other embodiments the member may be made of multiple materials. A lubricious material 215 may be on or impregnated in a portion of the member 214 (for example, on the convex side of the member 214). Alternatively, the lubricious material 215 may be on or impregnated in the entire outer surface of the member 214.

Member 214 at least partially encapsulates modules 210-212. Further, as will be described in greater detail below, lead connection modules 213 may be formed in member 214. Member may integrate modules 210-212 into a structure. Member 214 may provide a flexible structure that permits the device 501 to conform to a variety of implant locations.

In some embodiments, member 214 may be curved to match the shape of the location within a patient in which the device is being implanted. For example, implantation of modular implantable medical device 201 under the scalp of a patient may be accomplished if member 214 is concave (as viewed from the cranium) to substantially conform to the shape of the cranium of the patient and convex (as viewed from the scalp) to provide a smooth interface with the scalp or tissue near the scalp and thus reduces the likelihood of skin erosion and other problems associated with edges or protrusions pushing against the scalp. Concavity of modular implantable medical devices is described in greater detail in a commonly-assigned U.S. patent application Ser. No. 10/731,867, entitled "CONCAVITY OF AN IMPLANTABLE MEDICAL DEVICE,". Any number of shapes may be used to match a particular implantable medical device 201 to an implantation location for a device.

Member 214 may comprise a solid biocompatible elastomeric material that is soft and flexible such as silicone. In some embodiments, member 214 comprises two or more materials, and two or more components. For example, member may comprise one or more elastomeric components formed of an elastomeric material, such as silicone, and one or more non-elastomeric components formed of a non-elastomeric material, such as polysulfone, or a polyurethane such as Tecothane®, which is commercially available from Hermedics Polymer Products, Wilmington, Mass. The one or more elastomeric components may provide the overall shape and flexibility of modular implantable medical device 201, while the non-elastomeric components may provide structural integrity for modular implantable medical device 201, restrict intermodule motion within modular implantable medical device 201 to certain ranges, and form a part of the lead interconnection modules 213. Further detail regarding reduction of intermodule motion within modular implantable medical devices may be found in a commonly-assigned U.S. patent application Ser. No. 10/731,881, entitled "REDUCING RELATIVE INTERMODULE MOTION IN A MODULAR IMPLANTABLE MEDICAL DEVICE,".

FIGS. 3A-3F are schematic diagrams illustrating various arrangements of multiple modules within a modular implantable medical device 301 according to various embodiments of the present invention. In each of these embodiments, modular implantable medical device 301 has three modules as discussed above in reference to FIG. 2: a control module 210, a power source module 211, and a recharge module 212. These modules may be arranged into a variety of configurations, including those illustrated, as long as any required interconnections needed between the modules, e.g., coupling modules, may be routed within the device. The various embodiments include triangular configurations, in such as those shown in FIGS. 3A-C, and inline configurations, such as those shown in FIGS. 3D-F. The set of lead connection devices 313 may be located in various locations within the device as well.

Figure 3A:
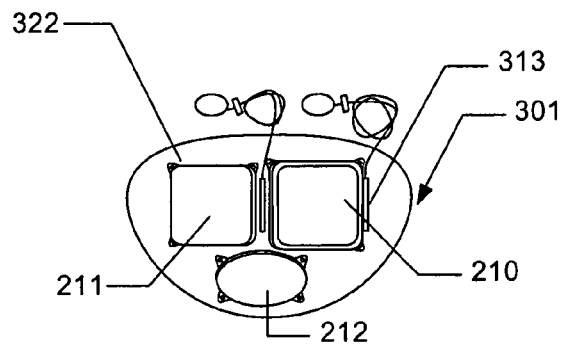
FIGS. 3A-3F are schematic diagrams illustrating various arrangements of modules within a modular implantable medical device according to various embodiments of the present invention.
Figure 3B:
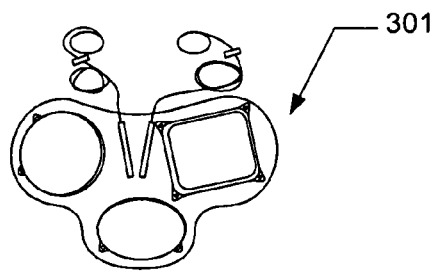
Figure 3C:
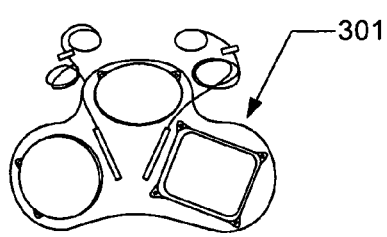
Figure 3D:
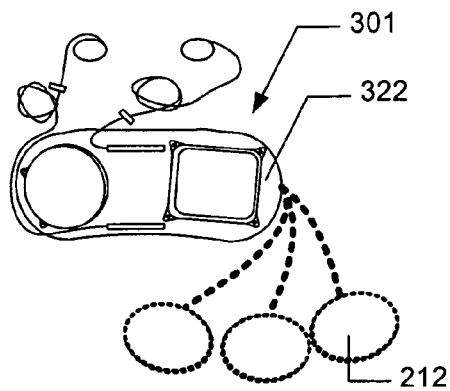
Figure 3E:
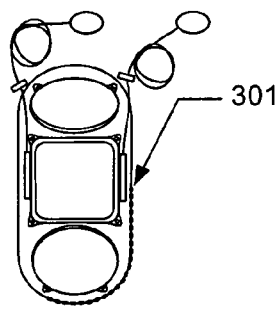
Figure 3F:
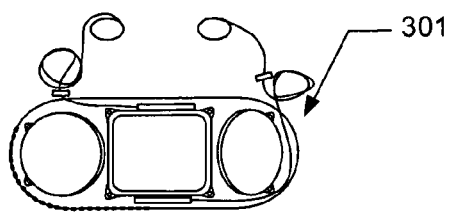

In some embodiments, such as those illustrated in FIGS. 3A-C and 3E-F, a member 322 at least partially encapsulates each of modules 210, 211 and 212. In other embodiments, such as that illustrated in FIG. 3D, at least one of the modules of modular IMD 301 is located outside of member 322. Module 212 located outside of member may, as shown in FIG. 3D, be tethered to member 322, allowing module 212 to be freely positioned some significant distance from member 322. Additional details relating to configurations of modules within a modular implantable medical device and tethering of modules of an implantable medical device may be found in a U.S. patent application Ser. No. 10/731,869, entitled "MODULAR IMPLANTABLE MEDICAL DEVICE,".

Figure 4A:
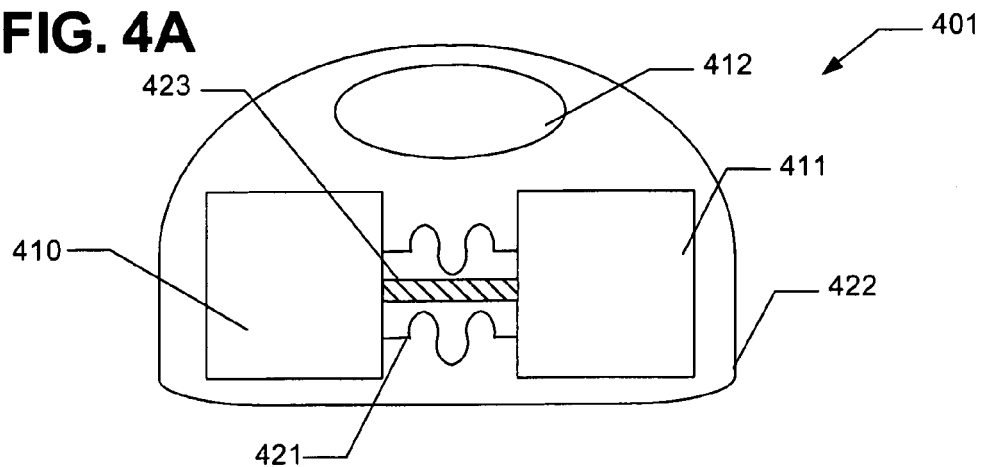
FIGS. 4A-4C are schematic diagrams illustrating the construction of a member of a modular implantable medical device according to the present invention.
Figure 4B:
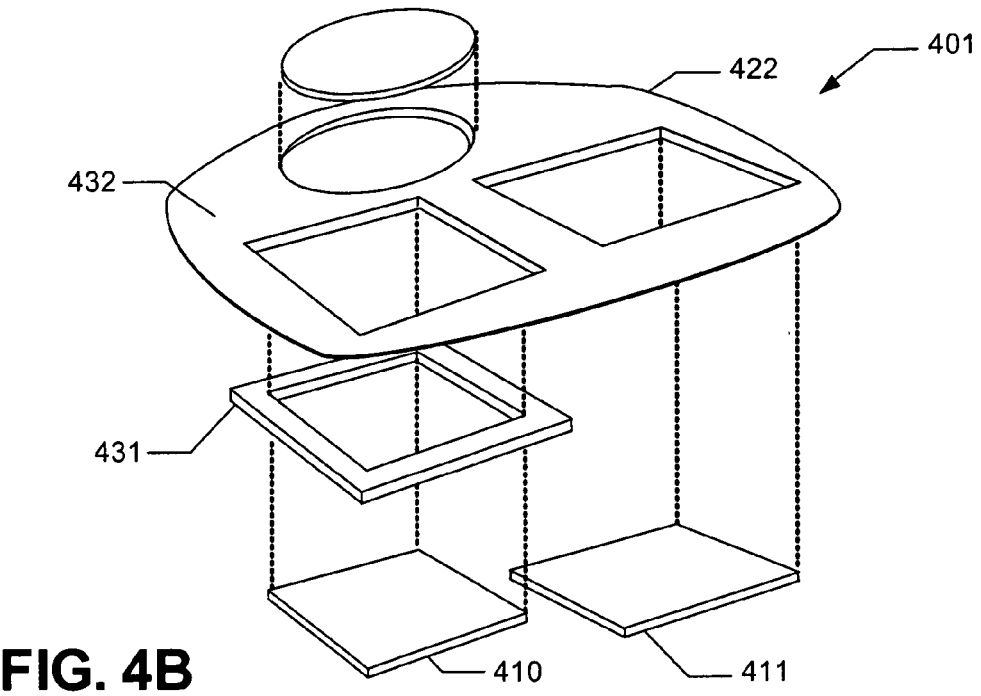
Figure 4C:
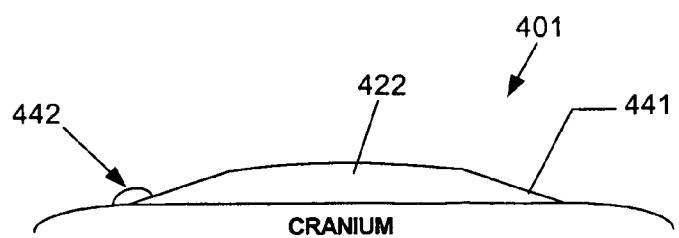

FIGS. 4A-4C are schematic diagrams illustrating a member 422 of a modular implantable medical device 401. FIG. 4A illustrates that the modular implantable medical device 401 comprises a set of modules 410-412, and a set of motion reduction elements 421 within member 422, such as motion reduction fibers connecting modules 410 and 411. Modules 410 and 411 are also coupled by a coupling module 423.

Because member 422 and coupling module 423 are flexible, member 422 and coupling module 423 may not provide sufficient motion reduction for the modules 410-412. Specifically, excessive relative motion between modules 410 and 411 may compromise the structural integrity of coupling module 424, which may lead to failure of modular implantable medical device 401. Motion reduction elements 421 are used to provide sufficient structural integrity to the device 401 once implanted into the patient 100 by restricting relative motion between modules 410 and 411 to certain directions or within certain ranges. Additional details regarding motion reduction elements 421 are described in co-pending and commonly assigned U.S. patent application Ser. No. 10/731,881, entitled "REDUCING RELATIVE INTERMODULE MOTION IN A MODULAR IMPLANTABLE MEDICAL DEVICE,".

FIG. 4B illustrates that the member 422 may include two or more components, each component made of a different material. In particular, FIG. 4B illustrates the member 422 includes an elastomeric component 430 and a non-elastomeric component 431. The non-elastomeric component 431 is typically shaped to surround at least one of modules 410-412, i.e., is located proximate to sides of at least one of modules 410-412. In some embodiments, a plurality of individual non-elastomeric components 431 surround respective modules 410-412. In other embodiments, a non-elastomeric component 431 surrounds a plurality of modules 410-412 to integrate the surrounded modules in a common, semi-rigid structure.

The one or more non-elastomeric components 431 may be used to contain one or more modules within elastomeric component 430. Specifically, the one or more non-elastomeric components 431 may be formed to hold modules 410-412 within respective positions within elastomeric component 430. Elastomeric component 430 may, as shown in FIG. 4B, at least partially encapsulate each of modules 410-412 and provide an desired form factor for a modular implantable medical device. In some embodiments, non-elastomeric elements 431 are fitted into an elastomeric component 430 to form the member 422 before the electronic modules 410-412 are inserted into respective locations within member 422 where they will be contained by non-elastomeric elements 431.

Generally, member 422 provides a number of functions in including attaching to modules and other elements to provide a smooth interface surface for the device as it interacts with the patient, and protecting electrical connections and feed thru wires needed to connect modules to external leads.

Member 422 may be constructed from a durometric specific material to provide a clinically desirable device. In addition, a material used to construct the member 422 may possess a thermal conductivity characteristic to either act as a heat sink if needed to dissipate heat from modules 410-412, or a material to act as an insulator to shield the patient 100 from any excess heat from modules 410-412. Because the implantable medical device 401 may be constructed from a large number of modules to perform a desired task, the materials selected for used in constructing the member 422 may vary as needed by each embodiment.

In embodiments in which member 422 is constructed of components 431 and 432, the device 401 may be fabricated by integrating components 431 and 432 to form the member 422, constructing the modules 410-412 and their respective connection modules 423, and constructing any motion reduction elements 421. Once all of these components are fabricated, the motion restriction elements 421 may be combined with the member 422, and the interconnected modules 410-412 may be inserted into the member 422 into respective positions where they are contained by components 431.

FIG. 4C illustrates that the member 422 provides sloped interface 441 between the modules within the device 401 and the patient's body components. In embodiments in which the device 401 is implanted within tight spaces, such as under the scalp, the sloped interface 441 provides a smooth transition between the body and the device modules 410-412. Protrusions are known to cause possible stress points for tissue that is located over implanted devices, which can, for example, lead to skin erosion in the case of a device implanted under the scalp. As such, the sloped interface 441 attempts to minimize the transition from the modules 410-412 and the edge of the device 401 to eliminate these points of stress. An angle of interface 442 from the patient's body and the sloped interface 441 is greater than 90 degrees. Angle 442 may be between 120 and 150 degrees, is preferably between 130 and 140 degrees, and is most preferably approximately 135 degrees.

Figure 5A:
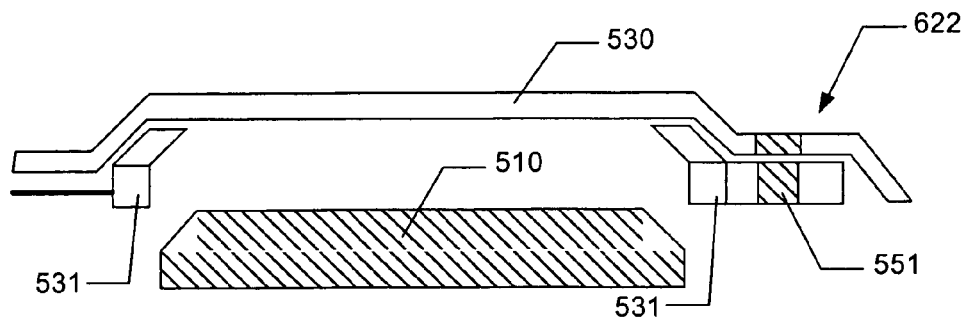
FIGS. 5A-5B are schematic diagrams illustrating the interaction of components of a member according to the present invention.
Figure 5B:
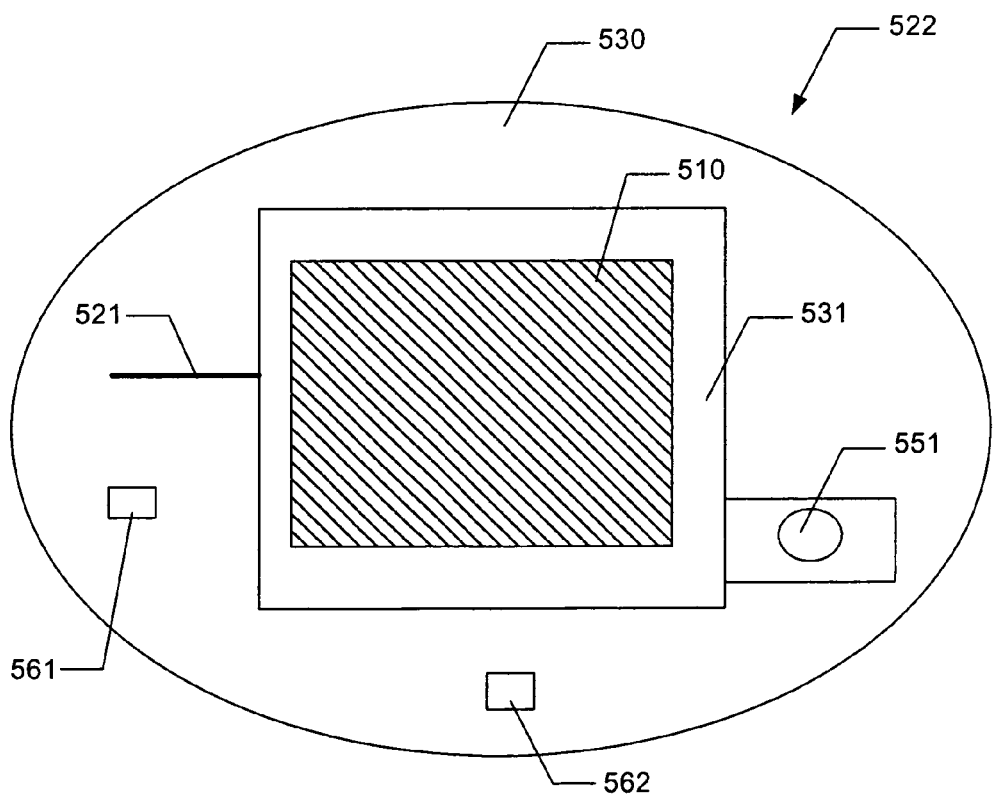

FIGS. 5A-5B are schematic diagrams illustrating the interaction of components of an implantable medical device that are part of a member. FIG. 5A provides a side cross-sectional view of a member 522 that includes an elastomeric component 530 and a non-elastomeric component 531 that interfaces with a control module 610. The non-elastomeric component 531 is shaped to mate with and surround the module 510, and may provide motion reduction for the module. Specifically, the non-elastomeric component 531 may be mechanically connected to at least one other module of a modular implantable medical device, e.g., to non-elastomeric components that surround other modules of an implantable medical device, by a motion reduction element 521. In other words, the member 522 encapsulates a plurality of modules in this embodiment, and each of the modules may be surrounded by a non-elastomeric component 531 that is connected to other non-elastomeric components by motion reduction elements 521.

A through hole 551 may be located through member 522, e.g., through elastomeric component 530 and non-elastomeric component 531, to provide an attachment point for the implantable medical device. In some embodiments, the implantable medical device may be secured in place using bone screws or similar attachment devices that secure the device to the patient. Such through holes 551 permit the device to be mechanically attached to the patient once the device is positioned at a desired location.

In addition, elastomeric component 530 is shown as completely encapsulating the modules and components within FIG. 5. However, in some embodiments, elastomeric component 530, like non-elastomeric component 531, may merely surround the module 510 but not cover the top of the module. Such an arrangement may render the profile of the overall device smaller. In such an alternate embodiment, a surface across the member and the electronics module 510 may minimize transition discontinuities to minimize profile changes that may interact with a patient after implantation. In other embodiments, one or both components 530 and 531 cover a top of module 510, or fully encapsulate module 510.

FIG. 5B illustrates a top view of the member 522 having an elastomeric component 530 that covers a non-elastomeric component 531 that surrounds the control module 510. The through hole 551 used as an attachment point is shown as part of the non-elastomeric component 531 that is covered by the elastomeric component 530. The shape of the non-elastomeric component 531 and control module 510 are shown as being rectangular in this embodiment. However, one skilled in the art will recognize that any shape for the non-elastomeric component 531 and control module 510 may be used without deviating from the spirit and scope of the present invention. Further, the shape of non-elastomeric component 531 need not be the same as that the shape of the component that it surrounds. The modules may be restrained within the member 522 using many restraint mechanisms known in the arts including attachment elements, adhesives, snap rings, and similar elements.

While the member 522 described above may be constructed from two different materials, a softer, more flexible elastomeric component 530 and one or more harder, more rigid non-elastomeric components 531, one skilled in the art may recognize that a member 522 may include a single component made of either class of material to provide the surface smoothing, module integration, and structural module restraint features described herein.

Finally, the member 522 may include several additional features unrelated to the above functions regarding the restraint and interconnection of multiple modules. In one embodiment, radio-opaque markers 561 and 562 may be imbedded within the member 522 to assist in determining an exact location of an implantable medical device within a patient. These radio-opaque markers 561 and 562 typically possess a non-symmetrical shape to permit registration and orientation of the device 501 from imaging of the markers. These radio-opaque markers may be constructed using barium and similar materials that permit such imaging. A telemetry and/or recharge coil may be embedded directly within the member 522.

It will be understood that a lubricious material may be disposed on or impregnated in at least a portion of an implantable medical device. In one embodiment, the lubricious material may be disposed on or impregnated in the housing. For example, a lubricious material may be disposed on or impregnated in the housing 90 in FIG. 1A. In another embodiment, the lubricious material may be disposed on or impregnated in the member. For example, the lubricious material may be disposed on or impregnated in the member 94 in FIG. 1B. Disposing a lubricious material on or impregnated in a medical device may facilitate insertion of the device into the implantation location. The lubricious material may also reduce post-implant friction between a portion of the medical device and the adjacent tissue.

It may be desirable to apply the lubricious material to less than the entire outer surface of the device. In the case of an implant between the brain and scalp, the lubricious material may be disposed on the side of the device facing the scalp and therefore provide for easier insertion of the device under the scalp as well as reduce post implantation friction between the device and the scalp or other tissue. For example, in the case of device 90 when implanted between the brain and scalp, the convex side of the member 94 may be coated with a lubricious material 98 to reduce friction between the scalp and the device 90.

Any known or future developed lubricious material, or combinations thereof, may be used. Preferably, the lubricious materials are medically suitable for inserting into a patient. Examples of suitable lubricous materials that may be disposed on at least a portion of a component of an implantable medical device include fluoroethylpolymer, polytetrafluoroethylene (PTFE), polyetheretherketone (PEEK), ethylene tetrafluoroethylene (ETFE), paralene, a hydrophilic polymer, and the like. Additional examples of suitable coating that may be applied include those described in the following patents and patent publications: US 20040030159; U.S. Pat. No. 6,558,734, U.S. Pat. No. 6,278,018; U.S. Pat. No. 6,603,040; U.S. Pat. No. 6,669,994; WO0121326; WO 0144174; and WO 2003055611. In an embodiment, the lubricious material is a hydrogel. The hydrogel may be a polyvinyl pyrrolidone (PVP) hydrogel, such as Medtronic's BIOGLIDE. In addition to facilitating insertion of a device, a lubricious material such as a hydrogel may prevent infection, thrombosis and formation of a fibrous capsule around the device. For example, BIOGLIDE technology has been shown to resist protein deposition, adherence of thrombosis, and reduce platelet and complement activation and may also inhibit tissue adherence.

Any known or future developed method for applying the lubricious material to either the housing or member may be utilized. In one embodiment, the lubricious material may be applied to the housing or member by being sprayed onto the surface of the housing or member. In another embodiment, the housing or member may be placed or dipped into the lubricious material allowing the lubricious material to be retained on or become impregnated in the housing or member.

In another embodiment the lubricious material may be the type of material that when activated by water or saline becomes slippery.

Figure 15:
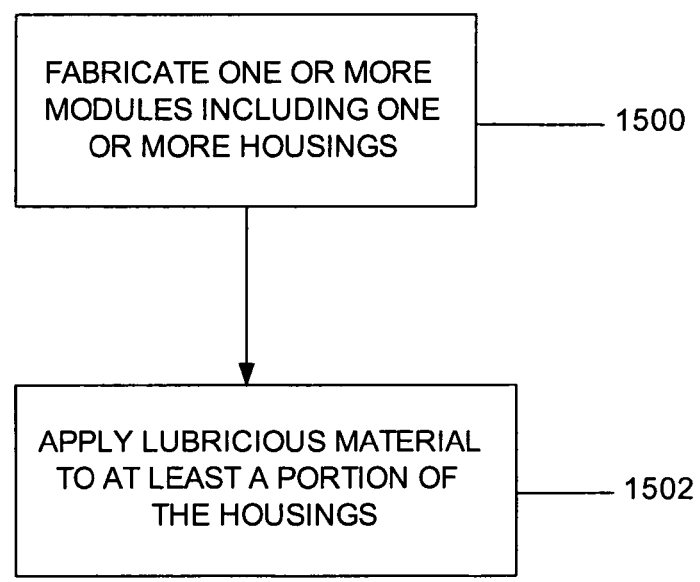
FIG. 15 is a flowchart illustrating a method of fabricating an implantable medical device including a lubricious material on or impregnated in the housing according to one embodiment of the present invention.

FIG. 15 is a flowchart illustrating one embodiment method of fabricating an implantable medical device including a lubricious material on the housing of the module. In this method, the module or plurality of modules of the device 80 are fabricated at step 1500. At step 1502 a lubricious material is applied to at least a portion of the housing 82 or multiple housings of the device 80. It should be understood that the lubricious material may be applied to the housing either prior to assembly of the components within the housing or after such assembly. Moreover, when multiple modules are used, the lubricious material may be applied to the housings before or after coupling the modules to each other.

Figure 16:
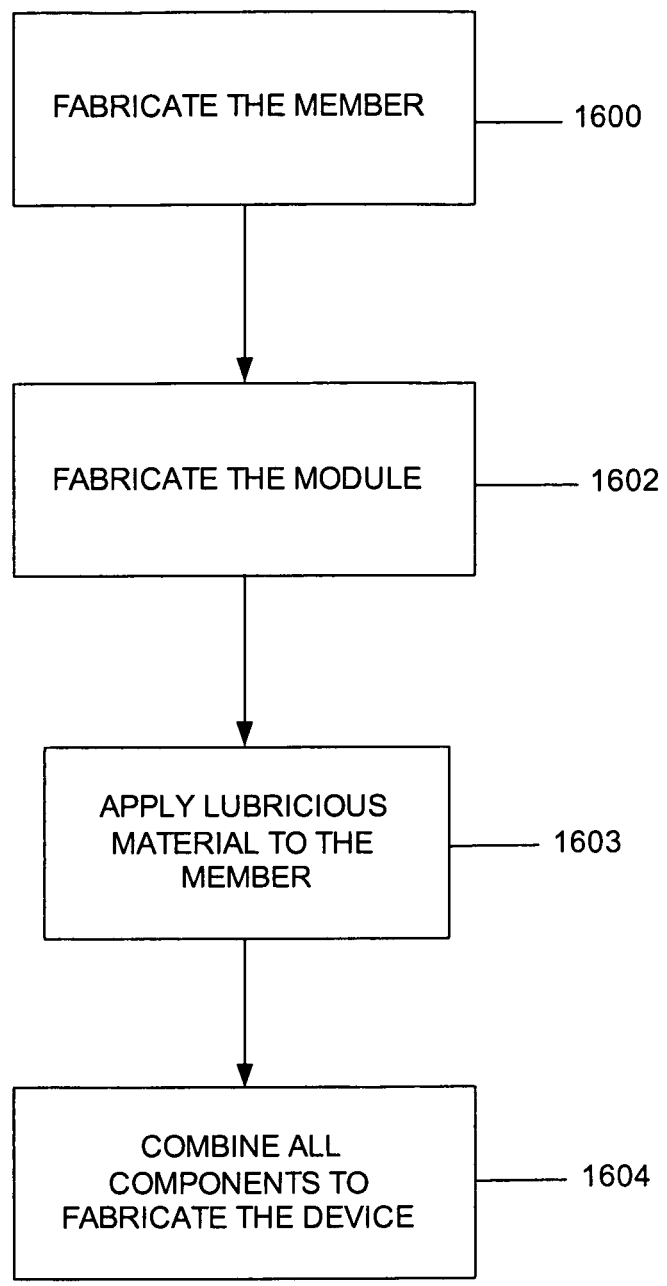
FIG. 16 is a flowchart illustrating a method of fabricating an implantable medical device including a lubricious material on a member according to one embodiment of the present invention.

FIG. 16 is a flowchart illustrating another embodiment method of fabricating an implantable medical device including a lubricious material on a member. In this method, the member is fabricated at step 1600. The fabrication of the member can be by any known or future developed method. At step 1602, a module is fabricated. At step 1604, a lubricious material is applied to the member. The components including the member and module are combined at step 1604. As described with regard to the process of FIG. 15, assembly and application of the lubricious material may be performed in any order.

Figure 6:
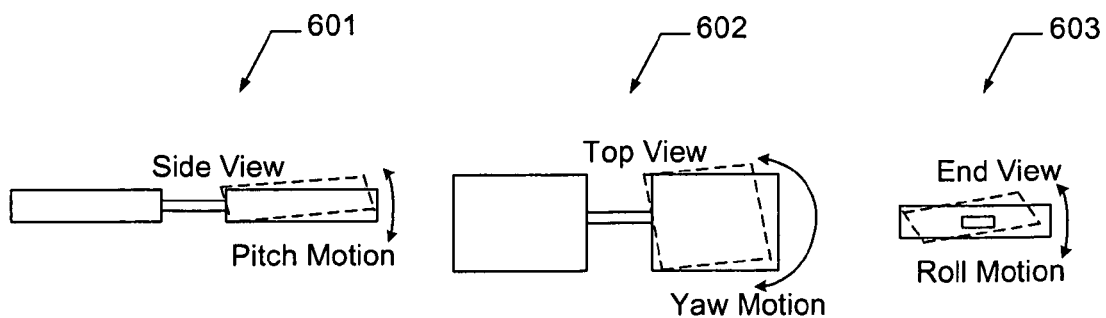
FIG. 6 is a schematic diagram illustrating the degrees of motion present in a modular implantable medical device.

FIG. 6 is a schematic diagram illustrating degrees of intermodular motion that may be present in modular implantable medical device. For any two modules within a distributed medical device, motion between the two modules may include pitch motion 601, yaw motion 602, and roll motion 603. For the set of motion reduction elements 621 discussed above, one or more of these three degrees of motion may be limited to prevent mechanical failures of interconnections between the modules during use of a modular implantable medical device. Specifically, modules of a modular implantable medical device may be connected by connector modules, which may be compromised by excessive intermodule motion. Such interconnect members are described in greater detail in commonly assigned U.S. patent application Ser. No. 10/731,881, entitled "REDUCING RELATIVE INTER-MODULE MOTION IN A MODULAR IMPLANTABLE MEDICAL DEVICE,".

Figure 7:
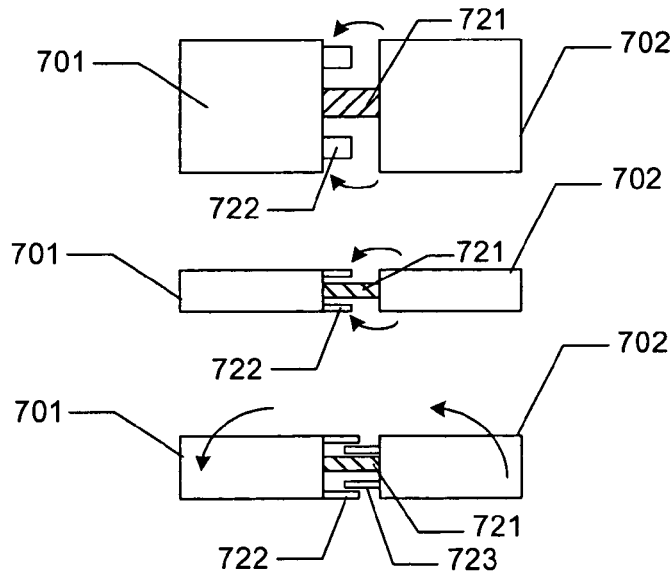
FIG. 7 is a schematic diagram illustrating motion reduction within various degrees of motion within a modular implantable medical device.

FIG. 7 is a schematic diagram illustrating motion reduction within various degrees of motion within a modular implantable medical device. For any two modules 701-702 within an implantable medical device, a connector module 721 may be used between the modules 701-702 to connect elements within these modules 701-702. Motion reduction elements 722 and 723 may be used to reduce inter-modular motion, and in some cases, to limit inter-modular motion to a range of motion.

Motion reduction elements 722 and 723 may be formed as part of non-elastomeric components 531 of a member 522 associated with each of modules 701 and 702. As shown in FIG. 7, motion reduction elements 722 and 723 allow free inter-modular motion within one of the degrees within a range. In some embodiments, one non-elastomeric component includes one or more motion reduction elements 722. In other embodiments, two non-elastomeric components 531 include motion reduction elements 722 and 723, respectively, which interact to reduce inter-modular motion.

A modular implantable medical device may include any number of motion reduction elements, which may take any of a variety of shapes. In some embodiments, motion reduction elements may be used in all axes to maximize the amount of motion reduction provided. The implantable medical device having multiple modules typically requires sufficient motion reduction to prevent undue mechanical stresses on interconnection connection member 721 between the modules 701-702 that may not be provided by a flexible member 522.

Additional details regarding the set of motion reduction elements 521 are described in co-pending and commonly assigned U.S. patent application Ser. No. 10/731,881, entitled "REDUCING RELATIVE INTERMODULE MOTION IN A MODULAR IMPLANTABLE MEDICAL DEVICE,".

Figure 8A:
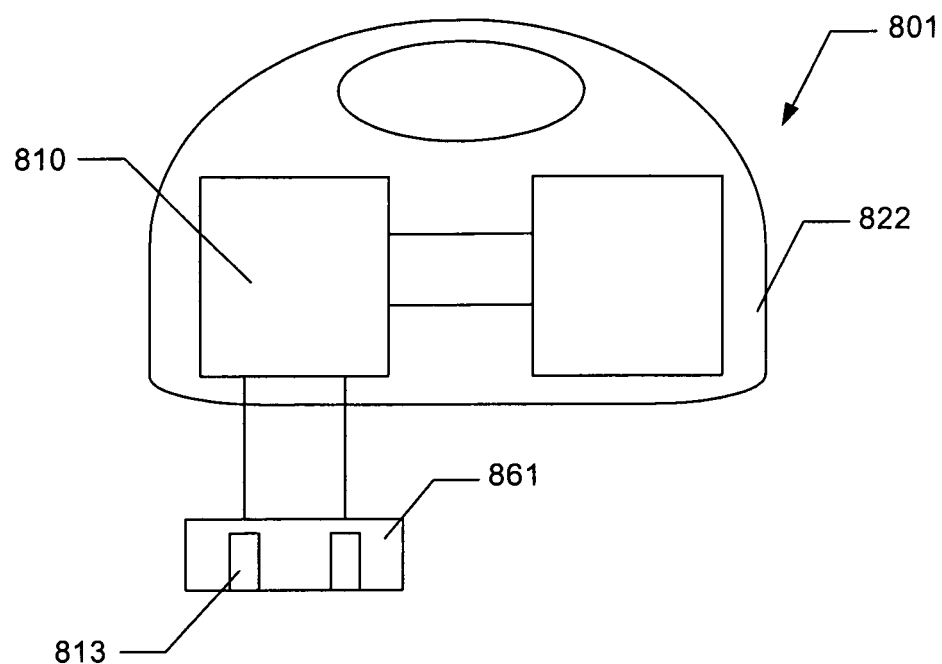
FIG. 8A-C are schematic diagrams illustrating example embodiments of modular implantable medical devices having lead management features.

FIG. 8A is a block diagram illustrating an example embodiment of a modular implantable medical device 801 having a tethered lead interconnect site 861 according to the present invention. A member 822 of implantable medical device 801 at least partially encapsulates and connects a plurality of modules 810-812 while not encapsulating lead connection modules 813 that are part of tethered lead interconnect site 861. In such embodiments, the implantation of device 801 would not require the insertion of external leads into the member 822. In addition, the external leads may be located a distance away from the device 801. Such an arrangement may assist in the management of the external leads as they are placed within the patient and routed to a device implantation location. Further, location of leads and connection site 861 away from member 822 may make it less likely that the leads will be damaged during a surgical explant procedure.

Figure 8B:
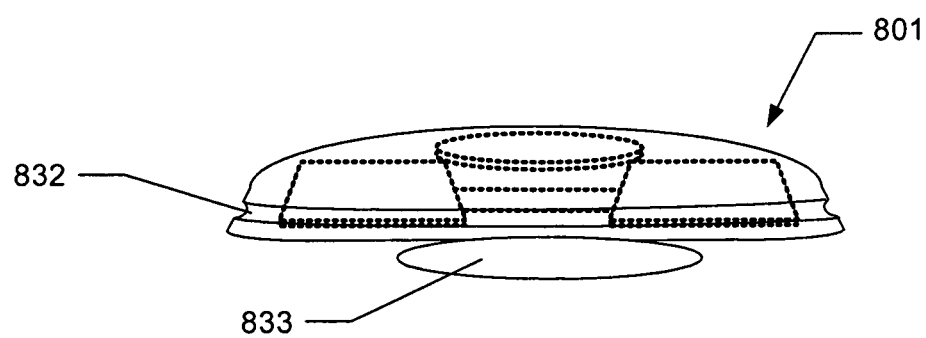
Figure 8C:
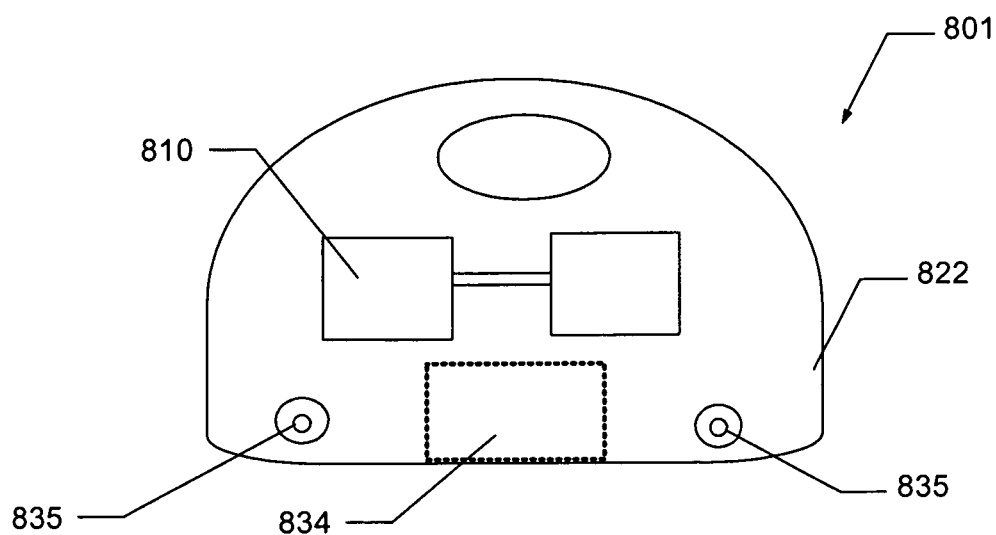

In alternate embodiments shown in FIGS. 8B-8C, member 822 may possess mechanical structures such as grooves 832, an externally attached pouch 833, or an integrated containment cavity 834 to contain and/or route the external leads away from the implantable medical device 801 in an efficient manner. In some embodiments, the external leads may possess a minimum length to provide a particular electrical characteristic for the implantable medical device 801. This minimum length may be greater than a distance needed by a particular patient for some implantation locations. These mechanical structures that assist in external lead management may accommodate any extra lead material that needs to be part of the device 801 in some implantation embodiments. Because the member may be spread over an area surrounding the modular device, the member may cover holes in the cranium formed to allow external leads to access the brain. Additional structures, including one or more cap structures 835 that secure a lead as it passes through the hole in the cranium may be an integral part of the member connector module 822.

Additional details regarding the lead connection modules described in co-pending and commonly assigned U.S. patent application Ser. No. 10/730,878, entitled "LEAD CONNECTION MODULE OF A MODULAR IMPLANTABLE MEDICAL DEVICE,".

Figure 9:
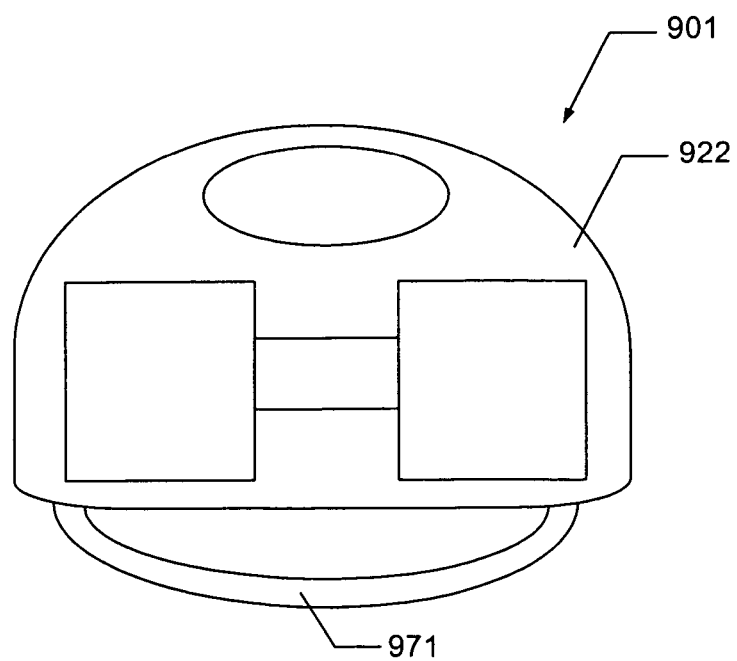
FIG. 9 is a schematic diagram illustrating an example embodiment of a modular implantable medical device having an access loop for removal.

FIG. 9 is a block diagram illustrating an example embodiment of a modular implantable medical device 901 having an access loop 971 for removal according to the present invention. Access loop 971 may be mechanically coupled to, or formed as a part of member connector module 922. This access loop 971 may be used to assist in the removal of the implantable medical device 901 at a point in time when the device 901 is no longer needed by the patient, or at a point in time when a particular device 901 needs to be replaced. The device 901 may be encapsulated within the patient 100 with scar tissue fibers such that physical effort will be required to remove the device 901 from its implantation location. This access loop 971 provides a clinician a removal assist structure to physically manipulate the implantable medical device 901 during its removal. This access loop 971 may also be useful during implantation of the device 901 as well as it provides a handle to manipulate the device 901 without handing the member 922 and its related modules. One skilled in the art will recognize that alternate embodiments for the access loop that may include removal handles, a strip cord and a reinforced opening within the member connector module to provide a mechanism to grasp the device to assist in removal.

Figure 10:
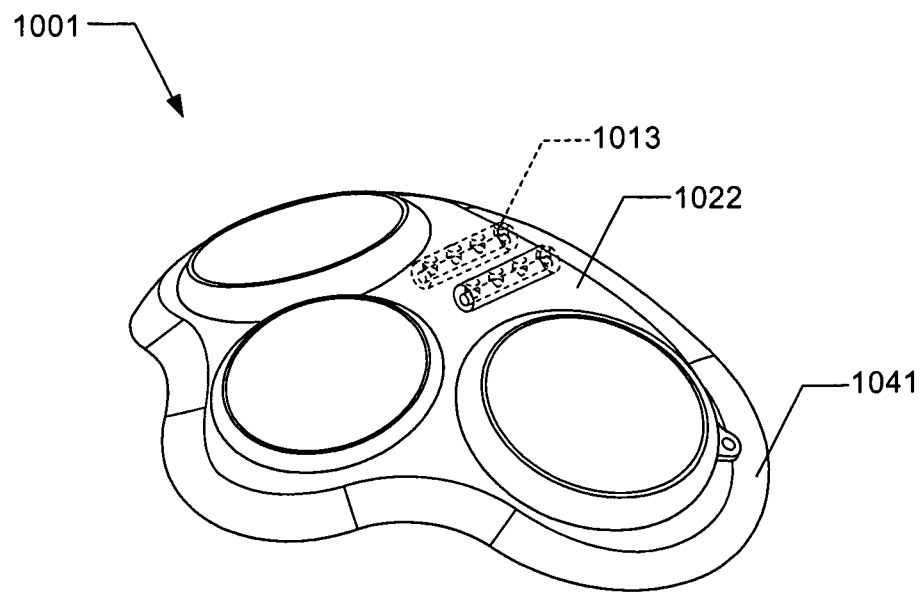
FIG. 10 is a schematic diagram illustrating a perspective view of an example embodiment of a modular implantable medical device having a triangular module arrangement.

FIG. 10 is a schematic diagram illustrating an example embodiment of a modular implantable medical device 1001 having a triangular module arrangement according to the present invention. In this embodiment, a triangular arrangement of modules is shown with a member 1022 that at least partially encapsulates all of the modules. Lead interconnection modules 1013 are located between the modules at a common location. Member 1022 provides a slope interface 1041.

Figure 11:
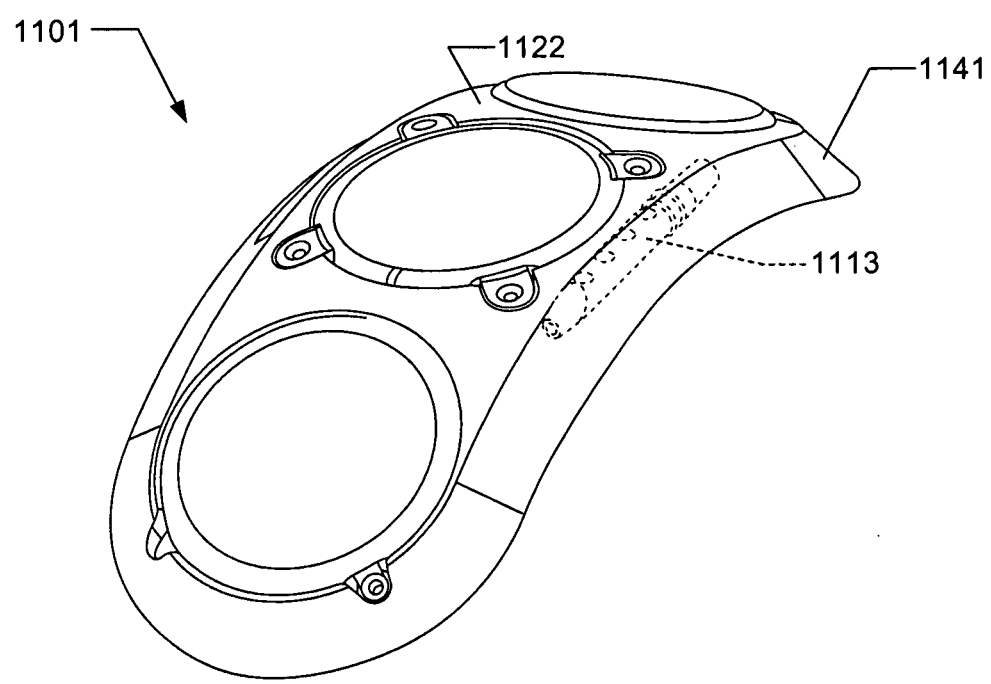
FIG. 11 is a schematic diagram illustrating a perspective view of an example embodiment of a modular implantable medical device having an inline module arrangement.

FIG. 11 is a schematic diagram illustrating an example embodiment of a modular implantable medical device 1101 having an inline module arrangement according to the present invention. In this embodiment, an inline arrangement of modules is shown with a member 1122 that at least partially encapsulates all of the modules. A lead interconnection module 1113 is located on one side of the member 1122. Member 1122 provides a slope interface 1141.

Figure 12:
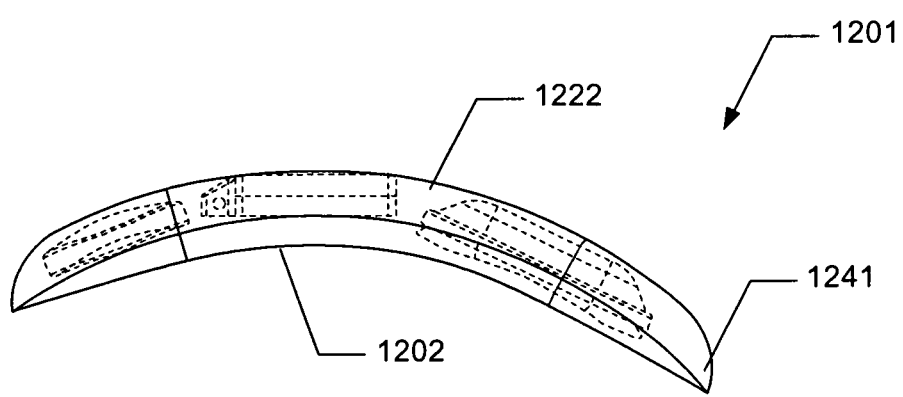
FIG. 12 is a schematic diagram illustrating side view of a modular implantable medical device having an inline module arrangement.

FIG. 12 is a schematic diagram illustrating side view of a multi-module implantable medical device having an inline module arrangement according to the present invention. The side view of the device 1201 shows an underside of the device 1202 that possess a curved shape to permit implantation at a location having a curved body structure.

Figure 13:
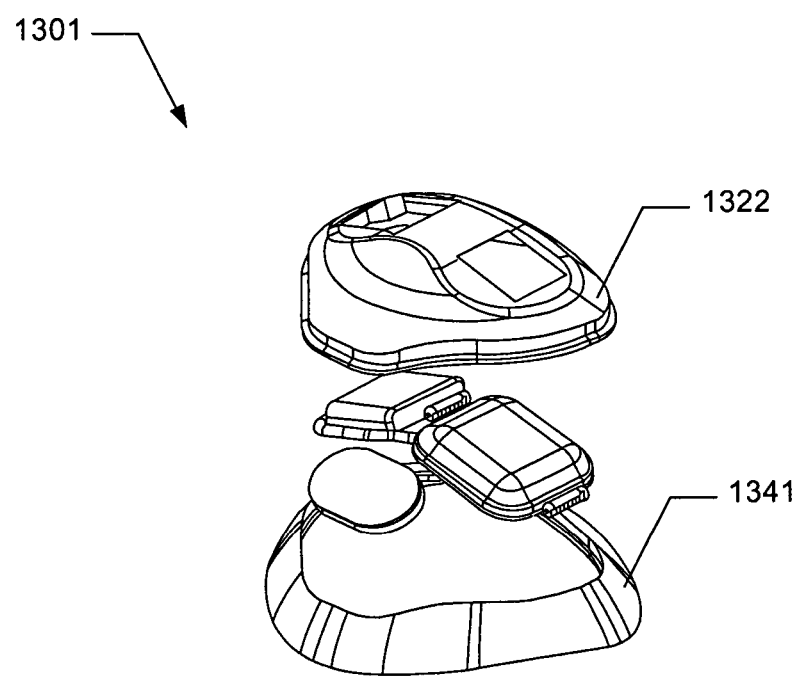
FIG. 13 is a schematic diagram illustrating an exploded view of a modular implantable medical device having a triangular module arrangement.

FIG. 13 is a schematic diagram illustrating an exploded view of a modular implantable medical device 1301 having a triangular module arrangement according to the present invention. In this embodiment, yet another triangular arrangement of modules is shown with a member 1322 at least partially encapsulating all of the modules. A slope interface element 1341 is shown surrounding the member 1322. In this embodiment, the slope interface element 1341 is shown as a separate physical structure, such as a flexible band, an o-ring, removable flexible flange, or a tapered outer contour element that surrounds the member 1322, rather than a tapered portion of member 1322. Slope interface element 1341 provides a desired sloped interface between the edge of the implantable medical device and the patient. In some embodiments, the shape and contour of slope interface element 1341 may be modified at the time of implantation to obtain a desired shape, or slope interface elements 1341 may be selected at the time of implantation from a variety of slope interface elements to provide a desired slope interface for a particular patient.

Figure 14:
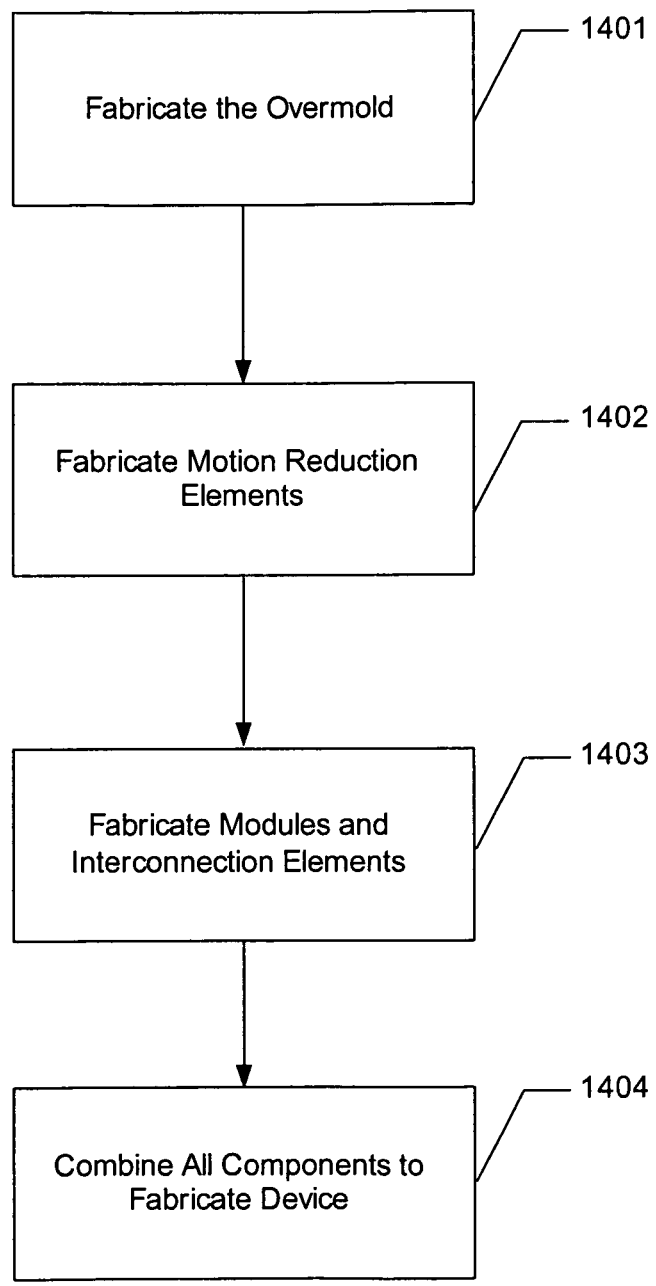
FIG. 14 is a flowchart illustrating a method of constructing an implantable medical device with a member according to the present invention.

FIG. 14 is a flowchart illustrating a method of constructing an implantable medical device with a member according to the present invention. An implantable medical device 401 may be fabricated by constructing the member 422 (1401) from a first and second component. As discussed above, member 422 may comprise two or more materials, and two or more components. For example, member may comprise one or more elastomeric components formed of an elastomeric material, such as silicone, and one or more non-elastomeric components formed of a non-elastomeric material. Once the member 422 is completed, the modules 410-412 with their respective connector modules 423 are constructed (1402). Next, any motion reduction elements 421 included in the device 401 are constructed. Once all of these components are fabricated, the motion restriction elements 421 may be combined with the member 422 (1403) and the interconnected modules 410-412 may be inserted (1404) into the member 422. From the combination of these components, the device 401 is formed.

It should be noted that the lubricious material may be on or impregnated in any of the embodiments of implantable medical devices provided even though such is not specifically called out in every Figure and accompanying description.

The foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto.

The invention claimed is:

1. An implantable medical device for implantation within a human body, the implantable medical device comprising:
    a first module comprising a first housing, wherein the first housing contains at least a portion of the electronics for providing monitoring of or therapy to a patient;
    a member at least partially encapsulating the first housing, wherein the member provides a smooth interface between at least a portion of the first housing and a tissue of the human body; and
    a lubricious material on or impregnated in at least a portion of the member, wherein the lubricious material is configured to reduce friction between the member and a tissue of the human body.

2. The implantable medical device of claim 1, wherein the lubricous material is only on or impregnated in one side of the member.

3. The implantable medical device of claim 1, wherein the implantable medical device is configured for implantation in a head of the human body.

4. The implantable medical device of claim 3, wherein the implantable medical device is configured for implantation between a scalp and a cranium of the human body.

5. The implantable medical device of claim 4, wherein a side of the member facing the scalp is substantially convex as viewed from the scalp.

6. The implantable medical device of claim 5, wherein the lubricious material is only on or impregnated in the substantially convex side of the member.

7. The implantable medical device of claim 1, wherein the member is flexible.

8. The implantable medical device of claim 1, wherein the member comprises an elastomeric material.

9. The implantable medical device of claim 8, wherein the elastomeric material is silicone.

10. The implantable medical device of claim 1, wherein the member comprises a non-elastomeric material.

11. The implantable medical device of claim 10, wherein the non-elastomeric material is one of a polysulfone and a polyurethane.

12. The implantable medical device of claim 1, further comprising a lead connection module within the member for connecting an external lead to electronics within the first module.

13. The implantable medical device of claim 1, wherein an edge of the member provides a sloped interface between an outer edge of the implantable medical device and a surface of a patient, and an angle between the edge and the surface of the patient is greater than 90 degrees.

14. The implantable medical device of claim 13, wherein the angle is within a range from 120 to 150 degrees.

15. The implantable medical device of claim 14, wherein the angle is approximately equal to 135 degrees.

16. The implantable medical device of claim 1, wherein the member comprises a material having a high thermal conductivity to act as a heat sink for thermal energy generated within the first module.

17. The implantable medical device of claim 1, wherein the member comprises a material having a low thermal conductivity to act as a shield of thermal energy generated within the first module.

18. The implantable medical device of claim 1, wherein the member includes a groove to hold external lead material.

19. The implantable medical device of claim 1, wherein the member includes a pouch to hold external lead material.

20. The implantable medical device of claim 1, wherein the member includes a through-hole to receive an attachment mechanism for attaching the implantable medical device to a patient.

21. The implantable medical device of claim 1, further comprising a second module coupled to the member, the second module comprising a second housing, wherein the member provides a smooth interface between the first and second housings and a tissue of the human body.

22. The implantable medical device of claim 21, wherein the lubricous material is only on or impregnated in one side of the member.

23. The implantable medical device of claim 21, wherein the implantable medical device is configured for implantation in a head of the human body.

24. The implantable medical device of claim 23, wherein the implantable medical device is configured for implantation between a scalp and a cranium of the human body.

25. The implantable medical device of claim 24, wherein a side of the member facing the scalp is substantially convex as viewed from the scalp.

26. The implantable medical device of claim 25, wherein the lubricious material is only on or impregnated in the substantially convex side of the member.

27. The implantable medical device of claim 21, wherein the member is flexible.

28. The implantable medical device of claim 21, wherein the member comprises an elastomeric material.

29. The implantable medical device of claim 28, wherein the elastomeric material is silicone.

30. The implantable medical device of claim 21, wherein the member comprises a non-elastomeric material.

31. The implantable medical device of claim 30, wherein the non-elastomeric material is one of a polysulfone and a polyurethane.

32. The implantable medical device of claim 21, further comprising a lead connection module within the member for connecting an external lead to electronics within the first module.

33. The implantable medical device of claim 21, wherein an edge of the member provides a sloped interface between an outer edge of the implantable medical device and a surface of a patient, and an angle between the edge and the surface of the patient is greater than 90 degrees.

34. The implantable medical device of claim 33, wherein the angle is within a range from 120 to 150 degrees.

35. The implantable medical device of claim 34, wherein the angle is approximately equal to 135 degrees.

36. The implantable medical device of claim 1, wherein the lubricious material is at least one of polyvinyl pyrrolidone (PVP) hydrogel, fluoroethylpolymer, polytetrafluoroethylene (PTFE), polyetheretherketone (PEEK), ethylene tetrafluoroethylene (ETFT), paralene, or a hydrophilic polymer.

37. An implantable medical device for implantation within a human body, the implantable medical device comprising:
- a first module comprising a first housing, wherein the first housing contains at least a portion of the electronics for providing monitoring of or therapy to a patient;
- a member at least partially encapsulating the first housing, wherein the member provides a smooth interface between at least a portion of the first housing and a tissue of the human body; and
- lubricating means on or impregnated in at least a portion of the member, wherein the lubricating means is configured to reduce friction between the member and the tissue of the human body.

38. An implantable medical device for implantation within a head of a human body, the implantable medical device comprising:
- a plurality of modules, each of modules comprising a respective one of a plurality of housings, wherein the plurality of housings contains at least a portion of the electronics for providing monitoring of or therapy to a patient;
- means for integrating the modules into a single structure, wherein the means for integrating at least partially encapsulates each of the housings and provides a smooth interface between the plurality of housings and a tissue of the human body; and
- lubricating means on or impregnated in at least a portion of the means for integrating, wherein the lubricating means is configured to reduce friction between the means for integrating and the tissue of the human body.

39. The implantable medical device of claim 38, wherein the means for integrating is flexible.

40. The implantable medical device of claim 38, wherein the means for integrating provides a sloped interface with a surface of a patient.

41. A method for fabricating an implantable medical device, the method comprising:
- fabricating a member configured to provide a smooth interface between the implantable medical device and a tissue of a human body;
- fabricating a first module;
- combining the member and the first module to at least partially encapsulate the first module with the member and construct the implantable medical device; and
- applying a lubricious material to the member for reducing friction between the member and the tissue.

42. The method of claim 41, wherein the lubricious material is at least one of polyvinyl pyrrolidone (PVP) hydrogel, fluoroethylpolymer, polytetrafluoroethylene (PTFE), polyetheretherketone (PEEK), ethylene tetrafluoroethylene (ETFT), paralene, or a hydrophilic polymer.

43. The method according to claim 41, wherein the member comprises a solid biocompatible elastomeric material that is flexible.

44. The method according to claim 41, wherein applying the lubricious material to the member comprises spraying the lubricious material onto the member.

45. The method according to claim 41, wherein applying the lubricious material to the member comprises placing the member into the lubricious material.

46. The method according to claim 41, wherein the implantable medical device is configured for implantation within a head of a patient.

47. The method according to claim 41, wherein the implantable medical device is configured for implantation between a scalp and a cranium of the patient.

* * * * *